United States Patent
Bossetti et al.

(10) Patent No.: US 11,980,480 B2
(45) Date of Patent: May 14, 2024

(54) CONTACT DETECTION FOR PHYSIOLOGICAL SENSOR

(71) Applicant: Apple Inc., Cupertino, CA (US)

(72) Inventors: Chad A. Bossetti, Colorado Springs, CO (US); Thomas J. Sullivan, San Jose, CA (US); Xiaoyu Guo, Santa Clara, CA (US); Paras Samsukha, San Jose, CA (US); Anirban Chatterjee, San Jose, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 17/821,433

(22) Filed: Aug. 22, 2022

(65) Prior Publication Data

US 2022/0401025 A1    Dec. 22, 2022

Related U.S. Application Data

(63) Continuation of application No. 16/565,090, filed on Sep. 9, 2019, now Pat. No. 11,478,193.

(Continued)

(51) Int. Cl.
 *A61B 5/00*    (2006.01)
 *A61B 5/24*    (2021.01)
(Continued)

(52) U.S. Cl.
 CPC .............. *A61B 5/6844* (2013.01); *A61B 5/24* (2021.01); *A61B 5/681* (2013.01); *A61B 5/7203* (2013.01);
(Continued)

(58) Field of Classification Search
 CPC ......... A61B 5/6844; A61B 5/24; A61B 5/681; A61B 5/7203; A61B 5/7228;
(Continued)

(56) References Cited

U.S. PATENT DOCUMENTS

| 5,483,261 A | 1/1996 | Yasutake |
| 5,488,204 A | 1/1996 | Mead et al. |

(Continued)

FOREIGN PATENT DOCUMENTS

| CN | 102694509 A | 9/2012 |
| CN | 103976730 A | 8/2014 |

(Continued)

OTHER PUBLICATIONS

Non-Final Office Action received for U.S. Appl. No. 16/565,090, dated Aug. 17, 2021, 15 pages.

(Continued)

*Primary Examiner* — Farhana A Hoque
(74) *Attorney, Agent, or Firm* — Kubota & Basol LLP

(57) ABSTRACT

Detecting user contact with one or more electrodes of a physiological signal sensor can be used to ensure physiological signals measured by the physiological signal sensor meet waveform characteristics (e.g., of a clinically accurate physiological signal). In some examples, a mobile and/or wearable device can comprise sensing circuitry, stimulation circuitry, and processing circuitry. The stimulation circuit can drive one or more stimulation signals on one or more electrodes, the resulting signal(s) can be measured (e.g., by the sensing circuitry), and the processing circuitry can determine whether a user is in contact with the electrode(s). Additionally or alternatively, in some examples, mobile and/or wearable device can comprise saturation detection circuitry, and the processing circuitry can determine whether the sensing circuitry is saturated.

20 Claims, 14 Drawing Sheets

Related U.S. Application Data

(60) Provisional application No. 62/729,590, filed on Sep. 11, 2018.

(51) Int. Cl.
*A61B 5/30* (2021.01)
*A61B 5/304* (2021.01)

(52) U.S. Cl.
CPC .......... *A61B 5/7228* (2013.01); *A61B 5/7475* (2013.01); *A61B 5/30* (2021.01); *A61B 5/304* (2021.01)

(58) Field of Classification Search
CPC .......... A61B 5/7475; A61B 5/30; A61B 5/304; A61B 5/28; A61B 5/256; A61B 5/332; A61B 5/339
See application file for complete search history.

(56) References Cited

U.S. PATENT DOCUMENTS

| | | | |
|---|---|---|---|
| 5,825,352 | A | 10/1998 | Bisset et al. |
| 5,835,079 | A | 11/1998 | Shieh |
| 5,880,411 | A | 3/1999 | Gillespie et al. |
| 6,188,391 | B1 | 2/2001 | Seely et al. |
| 6,310,610 | B1 | 10/2001 | Beaton et al. |
| 6,323,846 | B1 | 11/2001 | Westerman et al. |
| 6,690,387 | B2 | 2/2004 | Zimmerman et al. |
| 7,015,894 | B2 | 3/2006 | Morohoshi |
| 7,184,064 | B2 | 2/2007 | Zimmerman et al. |
| 7,663,607 | B2 | 2/2010 | Hotelling et al. |
| 8,479,122 | B2 | 7/2013 | Hotelling et al. |
| 9,542,820 | B2 * | 1/2017 | Moussette ............... G06F 3/016 |
| 9,629,564 | B2 | 4/2017 | Jonnada et al. |
| 10,213,602 | B2 | 2/2019 | Ironi et al. |
| 2006/0197753 | A1 | 9/2006 | Hotelling |
| 2011/0025348 | A1 | 2/2011 | Chetham et al. |
| 2011/0306892 | A1 | 12/2011 | Kim et al. |
| 2014/0094675 | A1 | 4/2014 | Luna et al. |
| 2014/0243633 | A1 | 8/2014 | Addison et al. |
| 2014/0303452 | A1 | 10/2014 | Ghaffari |
| 2014/0343392 | A1 | 11/2014 | Yang |
| 2015/0031964 | A1 | 1/2015 | Bly et al. |
| 2016/0028388 | A1 | 1/2016 | Kim et al. |
| 2017/0090599 | A1 | 3/2017 | Kuboyama et al. |
| 2017/0181644 | A1 | 6/2017 | Meer et al. |
| 2017/0340209 | A1 | 11/2017 | Klaassen et al. |
| 2017/0340258 | A1 | 11/2017 | Zou |
| 2017/0367600 | A1 | 12/2017 | Pemberton et al. |
| 2018/0028086 | A1 | 2/2018 | Cao et al. |
| 2020/0077954 | A1 | 3/2020 | Bossetti et al. |
| 2020/0077955 | A1 | 3/2020 | Shui et al. |
| 2023/0130899 | A1 | 4/2023 | Shui et al. |

FOREIGN PATENT DOCUMENTS

| | | |
|---|---|---|
| CN | 204765611 U | 11/2015 |
| CN | 105125207 A | 12/2015 |
| CN | 105310684 A | 2/2016 |
| CN | 205338955 U | 6/2016 |
| CN | 105980008 A | 9/2016 |
| CN | 106618569 A | 5/2017 |
| CN | 107106054 A | 8/2017 |
| CN | 108139792 A | 6/2018 |
| EP | 0072003 A2 | 2/1983 |
| EP | 2020600 A2 | 2/2009 |
| EP | 3089726 A2 | 11/2016 |
| EP | 3243430 A1 | 11/2017 |
| JP | 2000-163031 A | 6/2000 |
| JP | 2002-342033 A | 11/2002 |
| JP | 2016-54888 A | 4/2016 |
| KR | 10-2011-0135296 A | 12/2011 |
| WO | 2015/127119 A2 | 8/2015 |
| WO | 2016/040253 A1 | 3/2016 |
| WO | 2016/161152 A1 | 10/2016 |
| WO | 2017/072626 A1 | 5/2017 |

OTHER PUBLICATIONS

Non-Final Office Action received for U.S. Appl. No. 16/565,127, dated Dec. 22, 2021, 15 pages.
Non-Final Office Action received for U.S. Appl. No. 16/565,127, dated May 6, 2021, 14 pages.
Notice of Allowance received for U.S. Appl. No. 16/565,090, dated Jul. 1, 2022, 10 Pages.
Notice of Allowance received for U.S. Appl. No. 16/565,090, dated Mar. 30, 2022, 10 Pages.
Notice of Allowance received for U.S. Appl. No. 16/565,127, dated Jun. 13, 2022, 5 Pages.
Search Report received for Chinese Patent Application No. 201910858666.3, dated Dec. 20, 2021, 5 pages (2 pages of English Translation).
Lee et al., "A Multi-Touch Three Dimensional Touch-Sensitive Tablet", CHI'85 Proceedings, Apr. 1985, pp. 21-25.
Rubine, Dean, "Combining Gestures and Direct Manipulation", CHI'92, May 3-7, 1992, pp. 659-660.
Rubine, Dean H., "The Automatic Recognition of Gestures", CMU-CS-91-202, Submitted in Partial Fulfillment of the Requirements for the Degree of Doctor of Philosophy in Computer Science at Carnegie Mellon University, Dec. 1991, 285 pages.
Westerman, Wayne, "Hand Tracking, Finger Identification, and Chordic Manipulation on a Multi-Touch Surface", A Dissertation Submitted to the Faculty of the University of Delaware in Partial Fulfillment of the Requirements for the Degree of Doctor of Philosophy in Electrical Engineering, 1999, 363 pages.
Corrected Notice of Allowance received for U.S. Appl. No. 16/565,090, dated Sep. 14, 2022, 2 pages.
Notice of Allowability received for U.S. Appl. No. 16/565,127, dated Sep. 28, 2022, 2 pages.
Restriction Requirement received for U.S. Appl. No. 17/821,435, dated Sep. 13, 2023, 5 pages.

* cited by examiner

CONTACT DETECTION FOR PHYSIOLOGICAL SENSOR

CROSS-REFERENCE TO RELATED APPLICATIONS

This application is a continuation of U.S. application Ser. No. 16/565,090, filed Sep. 9, 2019, which claims the benefit of U.S. Provisional Application No. 62/729,590, filed Sep. 11, 2018, the contents of which are incorporated herein by reference in their entireties for all purposes.

FIELD

This relates generally to systems and methods of processing physiological signals, and more particularly, to detecting contact with one or more electrodes of a physiological sensor.

BACKGROUND

Electrocardiogram (ECG) waveforms can be generated based on the electrical activity of the heart during each heartbeat. The waveforms can be recorded from multiple electrical leads attached to various areas of a patient. For example, a 12-lead ECG system with a group of ten measurement electrodes that can be placed across the patient's chest, and a group of ten measurement electrodes that can be attached to the patient's limbs. The measurement electrodes for ECG data acquisition can include a conducting or electrolytic gel (e.g., Ag/AgCl gel) to provide a continuous, electrically-conductive path between the skin and the electrodes. Such "wet" electrodes can reduce the impedance at the electrode-skin interface, thereby facilitating the acquisition of a low-noise ECG signal. All of the measurement electrodes can be connected to a device where signals from the measurement electrodes can be transmitted for storage, processing, and/or displaying. Devices with numerous "wet" electrodes coupled to the user's chest and limbs are invasive, may be difficult to operate for a layperson, and the result ECG waveform may be difficult to interpret. As a result, ECG measurements and analysis may limit the usage of ECG devices to a medical setting or by medical professionals.

One method of measuring an ECG signal is to use dry electrodes that make contact with two areas of a patient, oftentimes on opposite sides of the heart (e.g., on each of the user's hands). On a mobile device (e.g., a wearable device), ECG electrodes can be placed on the device such that the user can make contact with two electrodes. Reliable contact may be required to generate accurate ECG waveforms.

SUMMARY

This relates to devices and methods of using a mobile or wearable device to detect a user contact with one or more electrode(s) for the measurement of a physiological signal (e.g., ECG signals) for processing and/or display on the mobile or wearable device. The mobile or wearable device can comprise one or more measurement electrodes, one or more reference electrodes, and processing circuitry coupled to the electrodes. In some examples, the device can include a stimulation circuit. The stimulation circuit can drive a stimulation signal on one of the measurement electrodes. In some examples, the processing circuitry can detect a signal resulting from the stimulation signal and, based on the detected signal, determine whether a user is in contact with the one or more measurement electrodes. In some examples, upon determining that a user is in contact with the one or more measurement electrodes, the processing circuitry can measure a physiological signal of the user.

In some examples, the stimulation circuit can drive a first stimulation signal on one of the electrodes (e.g., a first measurement electrode) and a second stimulation signal on a second of the electrodes (e.g., a first reference electrode). In some examples, the processing circuitry can detect one or more signals resulting from the first and second stimulation signals and based on the one or more detected signal, determine whether a user is in contact with the one or more electrodes. In some examples, upon determining that a user is in contact with the one or more electrodes, the processing circuitry can measure a physiological signal of the user. In some examples, while measuring the physiological signal of the user, the simulation circuit can drive one or more of the electrodes to determine whether the user maintains contact with the one or more electrodes during the measurement of the physiological signal of the user.

DETAILED DESCRIPTION

In the following description of examples, reference is made to the accompanying drawings which form a part hereof, and in which it is shown by way of illustration specific examples that can be practiced. It is to be understood that other examples can be used and structural changes can be made without departing from the scope of the disclosed examples.

This relates to devices and methods of using a mobile or wearable device to detect a user contact with one or more electrode(s) for the measurement of a physiological signal (e.g., ECG signals) for processing and/or display on the mobile or wearable device. The mobile or wearable device can comprise one or more measurement electrodes, one or more reference electrodes, and processing circuitry coupled to the electrodes. In some examples, the device can include a stimulation circuit. The stimulation circuit can drive a stimulation signal on one of the measurement electrodes. In some examples, the processing circuitry can detect a signal resulting from the stimulation signal and, based on the detected signal, determine whether a user is in contact with the one or more measurement electrodes. In some examples, upon determining that a user is in contact with the one or more measurement electrodes, the processing circuitry can measure a physiological signal of the user.

In some examples, the stimulation circuit can drive a first stimulation signal on one of the electrodes (e.g., a first measurement electrode) and a second stimulation signal on a second of the electrodes (e.g., a first reference electrode). In some examples, the processing circuitry can detect one or more signals resulting from the first and second stimulation signals and based on the one or more detected signal, determine whether a user is in contact with the one or more electrodes. In some examples, upon determining that a user is in contact with the one or more electrodes, the processing circuitry can measure a physiological signal of the user. In some examples, while measuring the physiological signal of the user, the simulation circuit can drive one or more of the electrodes to determine whether the user maintains contact with the one or more electrodes during the measurement of the physiological signal of the user.

Figure 1A:
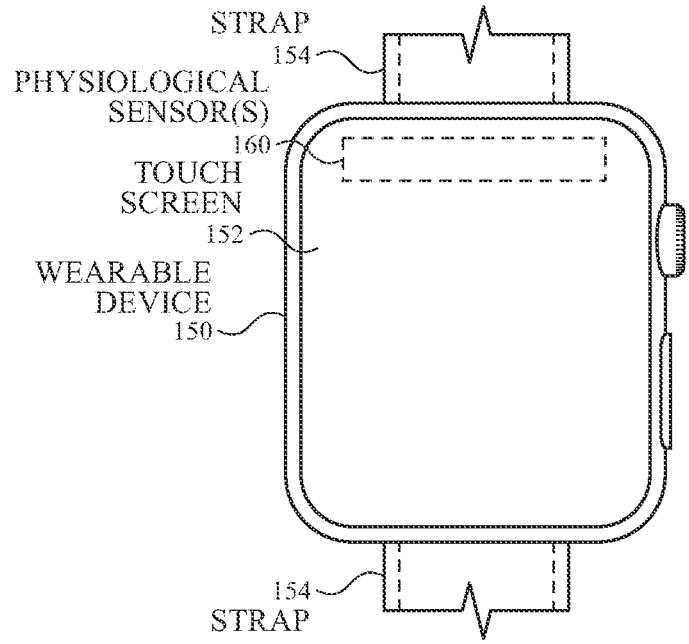
FIGS. 1A-1B illustrate example systems including a physiological sensor and in which contact detection according to examples of the disclosure may be implemented.
Figure 1B:
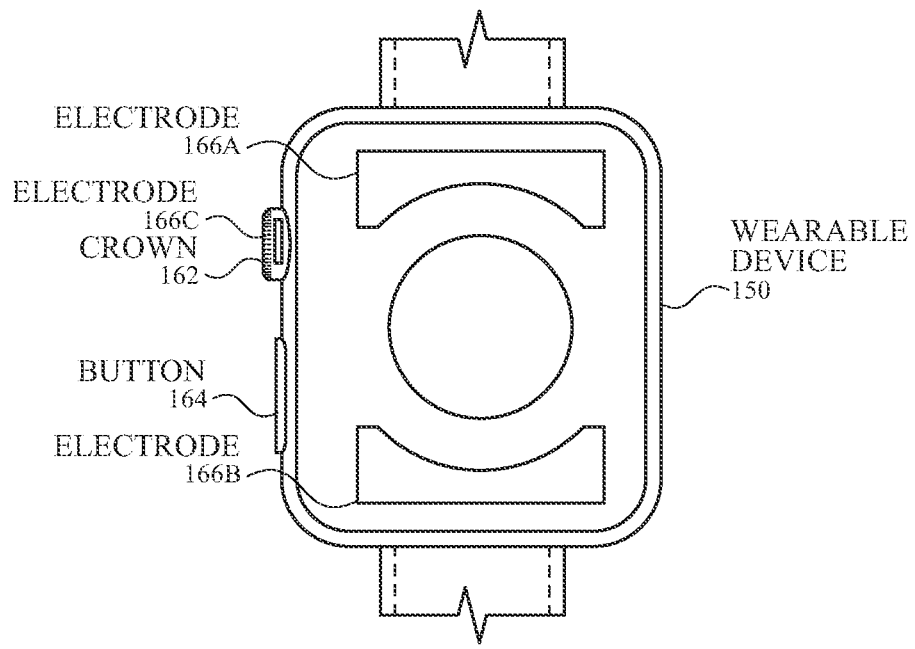

FIGS. 1A-1B illustrate example systems including a physiological sensor and in which contact detection according to examples of the disclosure may be implemented. FIG. 1A illustrates an example wearable device 150 (e.g., a watch) that includes an integrated touch screen 152 and physiological sensor(s) 160 (e.g., an ECG sensing system including one or more measurement electrodes, one or more reference electrodes, and processing circuitry coupled to the electrodes). Wearable device 150 can be attached to a user using a strap 154 or any other suitable fastener. FIG. 1B illustrates an example view of the back side of wearable device 150 that includes electrodes 166A-C of physiological sensor 160. Physiological sensor 160 can include electrode 166C implemented in crown 162 of wearable device 150, an electrode implemented in button 164 of wearable device 150 (not shown), electrode 166A on the back side of wearable device 150 and/or electrode 166B on the backside of wearable device 150. In some examples, the physiological sensor 160 can include a measurement electrode (e.g., electrode 166C in crown 162), a first reference electrode (e.g., electrode 166A on the backside of wearable device 150) and a second, ground reference electrode (electrode 166B on the backside of wearable device 150). In some examples, the physiological sensor 160 can include a measurement electrode in button 164 in addition to or instead of measurement electrode 166C in crown 162. In some examples, the physiological sensor 160 can include more than one measurement electrode and more than two reference electrodes. It is understood that the above physiological sensor(s) can be implemented in other wearable and non-wearable devices, including dedicated devices for the acquisition and/or processing of physiological signals (e.g., ECG signals). It is understood that although mobile device 136 and wearable device 150 include a touch screen, the display of physiological signals described herein can be performed on a touch-sensitive or non-touch-sensitive display of the device including physiological sensor(s) 160 of a separate device or of a standalone display. Additionally it is understood that although the disclosure herein primarily focuses on ECG signals, the disclosure can also be applicable to other physiological signals.

In some examples, the electrodes of physiological sensors 160 can be dry electrodes which can be measurement electrodes configured to contact a skin surface and capable of obtaining an accurate signal without the use of a conducting or electrolytic gel. In some variations, one or more reference electrodes may be located on a wrist-worn device, such as a bracelet, wrist band, or watch, such that the reference electrodes can contact the skin in the wrist region, while one or more measurement electrodes can be configured to contact a second, different skin region (e.g., a finger of a hand opposite the wrist wearing the wrist-worn device). In some examples, the measurement electrode(s) can be located on a separate component from the reference electrode(s). In some examples, some or all of the measurement electrode(s) can be located on a wrist or finger cuff, a fingertip cover, a second wrist-worn device, a region of the wrist-worn device that can be different from the location of the reference electrode(s), and the like. In some examples, one or more electrodes (e.g., reference electrode or measurement electrode) may be integrated with an input mechanism of the device (e.g., a rotatable input device, a depressible input device, or a depressible and rotatable input device, for example), as shown in FIG. 1B. One or more electrical signals at the one or more measurement (and/or reference) electrodes can be measured and processed as described in more detail herein.

Figure 2:
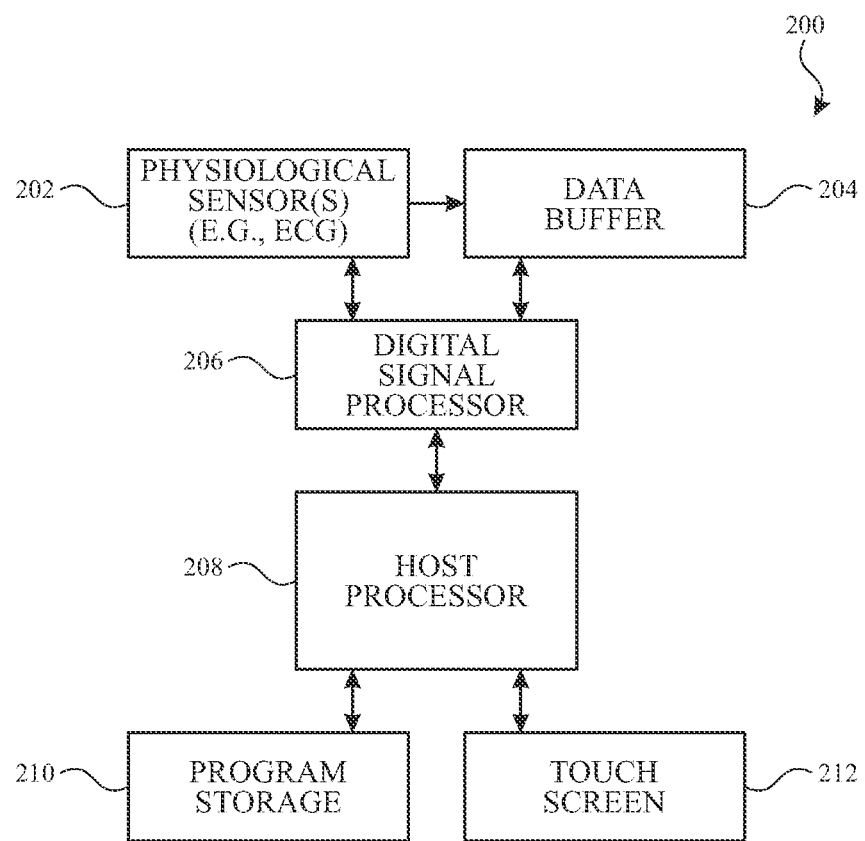
FIG. 2 illustrates a block diagram of an example computing system that illustrates one implementation of physiological signal processing according to examples of the disclosure.

FIG. 2 illustrates a block diagram of an example computing system 200 that illustrates one implementation of physiological signal processing according to examples of the disclosure. Computing system 200 can be included in, for example, wearable device 150 or any mobile or non-mobile, wearable or non-wearable computing device for physiological signal analysis and/or display. Computing system 200 can include one or more physiological sensors 202 (e.g., ECG sensors) including one or more electrodes to measure electrical signals (e.g., ECG signals) from a person contacting the ECG sensor(s) electrodes, data buffer 204 (or other volatile or non-volatile memory or storage) to store temporarily (or permanently) the physiological signals from the physiological sensors 202, digital signal processor (DSP) 206 to analyze and process the physiological signals, host processor 208, program storage 210, and touch screen 212 to perform display operations (e.g., to display real time ECG signals). In some examples, touch screen 212 may be replaced by a non-touch sensitive display.

Host processor 208 can be connected to program storage 210 to execute instructions stored in program storage 210 (e.g., a non-transitory computer-readable storage medium). Host processor 208 can, for example, provide control and data signals to generate a display image on touch screen 212, such as a display image of a user interface (UI). Host processor 208 can also receive outputs from DSP 206 (e.g., an ECG signal) and performing actions based on the outputs (e.g., display the ECG signal, play a sound, provide haptic feedback, etc.). Host processor 208 can also receive outputs (touch input) from touch screen 212 (or a touch controller, not-shown). The touch input can be used by computer programs stored in program storage 210 to perform actions that can include, but are not limited to, moving an object such as a cursor or pointer, scrolling or panning, adjusting control settings, opening a file or document, viewing a menu, making a selection, executing instructions, operating a peripheral device connected to the host device, answering a telephone call, placing a telephone call, terminating a telephone call, changing the volume or audio settings, storing information related to telephone communications such as addresses, frequently dialed numbers, received calls, missed calls, logging onto a computer or a computer network, permitting authorized individuals access to restricted areas of the computer or computer network, loading a user profile associated with a user's preferred arrangement of the computer desktop, permitting access to web content, launching a particular program, encrypting or decoding a message, and/or the like. Host processor 220 can also perform additional functions that may not be related to touch processing and display.

Note that one or more of the functions described herein, including contact detection, saturation detection and/or the processing of physiological signals, can be performed by firmware stored in memory (e.g., in DSP 206) and executed by one or more processors (in DSP 206), or stored in program storage 210 and executed by host processor 208. The firmware can also be stored and/or transported within any non-transitory computer-readable storage medium for use by or in connection with an instruction execution system, apparatus, or device, such as a computer-based system, processor-containing system, or other system that can fetch the instructions from the instruction execution system, apparatus, or device and execute the instructions. In the context of this document, a "non-transitory computer-readable storage medium" can be any medium (excluding signals) that can contain or store the program for use by or in connection with the instruction execution system, apparatus, or device. The computer-readable storage medium can include, but is not limited to, an electronic, magnetic, optical, electromagnetic, infrared, or semiconductor system, apparatus or device, a portable computer diskette (magnetic), a random access memory (RAM) (magnetic), a read-only memory (ROM) (magnetic), an erasable programmable read-only memory (EPROM) (magnetic), a portable optical disc such a CD, CD-R, CD-RW, DVD, DVD-R, or DVD-RW, or flash memory such as compact flash cards, secured digital cards, USB memory devices, memory sticks, and the like.

The firmware can also be propagated within any transport medium for use by or in connection with an instruction execution system, apparatus, or device, such as a computer-based system, processor-containing system, or other system that can fetch the instructions from the instruction execution system, apparatus, or device and execute the instructions. In the context of this document, a "transport medium" can be any medium that can communicate, propagate or transport the program for use by or in connection with the instruction execution system, apparatus, or device. The transport medium can include, but is not limited to, an electronic, magnetic, optical, electromagnetic or infrared wired or wireless propagation medium.

It is to be understood that the computing system 200 is not limited to the components and configuration of FIG. 2, but can include other or additional components (or omit components) in multiple configurations according to various examples. For example, an analog-to-digital converter (ADC) may be added between physiological sensor 202 and DSP 206 to convert the signals to the digital domain, or touch screen 212 can be omitted and the ECG signal or other information from the analysis and processing can be relayed to another device (e.g., a tablet, laptop, smartphone, computer, server, etc.) via wired or wireless connection that can include a display or other feedback mechanism for outputting a visual representation of the data or other notifications or information. Additionally, the components of computing system 200 can be included within a single device, or can be distributed between multiple devices.

Returning back to physiological sensor(s) 202, the mobile or wearable device (or other device) may comprise one or more of measurement electrodes and one or more reference electrodes. Physiological sensors 202 can be in communication with DSP 206 to acquire physiological signals and transmit the signals to DSP 206. In some examples, the physiological signals can be acquired by data buffer 204 and the DSP 206 can acquire a buffered sample of the physiological waveform (e.g., 3 second sample, 5 second sample, 10 second sample, 30 second sample, 60 second sample). In some examples, data buffer 204 can be implemented as part of DSP 206. It should be understood that although a DSP is described, other processing circuits could be used to implement the analysis and processing described herein including a microprocessor, central processing unit (CPU), programmable logic device (PLD), and/or the like.

Although the examples and applications of contact detection and processing devices and methods are described in the context of generating a complete ECG waveform, it should be understood that the same or similar devices and methods may be used to collect and process data from the plurality of measurement electrodes and may or may not generate an ECG waveform. For example, the signals from the physiological sensors 202 may facilitate the monitoring of certain cardiac characteristics (e.g., heart rate, arrhythmias, changes due to medications or surgery, function of pacemakers, heart size, etc.) and/or ECG waveform characteristics (e.g., timing of certain waves, intervals, complexes of the ECG waveform) by the DSP and/or user without generating a complete ECG waveform. In some examples, the controller may generate a subset of the ECG waveform (e.g., one or more of the P wave, QRS complex, PR interval, T wave, U wave). Moreover, examples of the disclosure include contact detection and processing devices and methods configured for other types of physiological signal measurements including, but not limited to, EEG and EMG measurements or optical determination of heart rate.

Figure 3A:
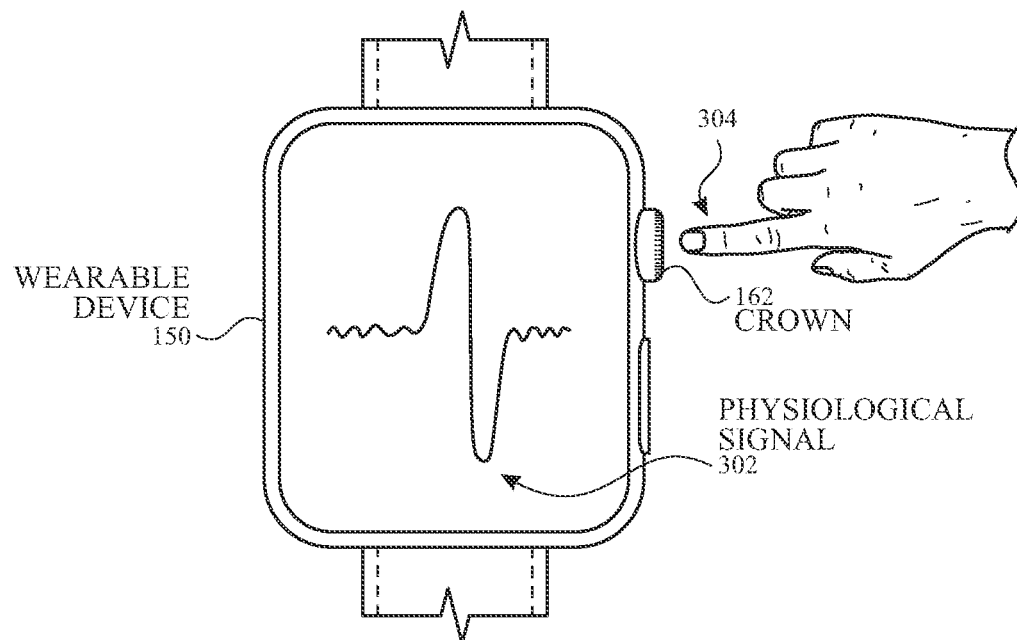
FIGS. 3A-3B illustrate example systems of measuring physiological signals according to examples of the disclosure.
Figure 3B:
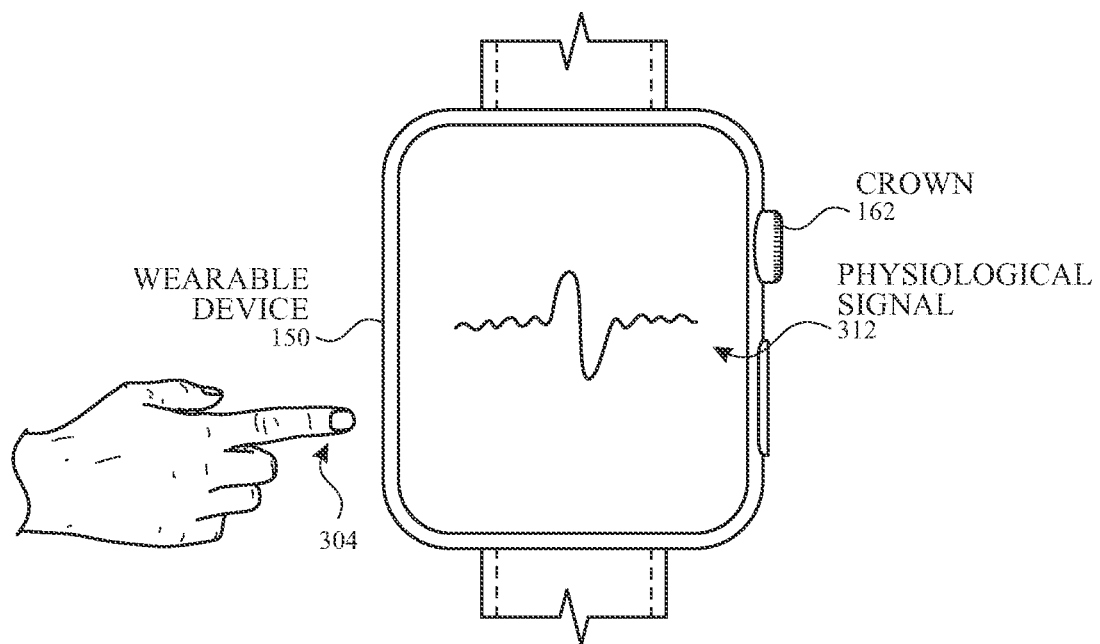

FIGS. 3A-3B illustrate example systems of measuring physiological signals (e.g., an ECG waveform) according to examples of the disclosure. In FIG. 3A, wearable device 150 can be worn on the wrist of a user. In some examples, reference electrodes 166A and 166B on the back side of wearable device 150 can contact the wrist of the user when worn. In some examples, wearable device 150 can measure a physiological signal when a user contacts measurement electrode 166C on crown 162 of wearable device 150 with finger 304 (e.g., of a hand opposite the wrist wearing the wrist-worn device). Physiological signal 302 can be measured in response to the contact of finger 304 with measurement electrode 166C (and the contact between the wrist and reference electrodes 166A and 166B). In some examples, the measured physiological signal 302 can be a clinically accurate waveform (e.g., meets the specifications for a clinically accurate waveform) due to the reliable contact with measurement electrode 166C (and reliable contact with reference electrodes 166A and/or 166B). FIG. 3B illustrates a user contact of finger 304 with the housing of wearable device 150 instead of crown 162. In some examples, physiological signal 312 can be acquired due to coupling between the housing of wearable device 150 and the measurement electrode 166C. In some examples, physiological signal 312 can have a similar morphology as physiological signal 302, but physiological signal 312 can be attenuated as compared to physiological signal 302 (e.g., 5%, 10%, 20% attenuation, etc.). In some examples, physiological signal 312 may be unstable, noisy, and/or the amplitude and attenuation can vary non-deterministically. In some examples, the measured physiological signal 312 may not be a clinically accurate waveform (e.g., does not conform to the specifications for a clinically accurate waveform) and can be difficult to interpret or lead to misinterpretation of the physiological signal (e.g., as compared with physiological signal 302). Contact detection, as described herein, can be used to avoid generating and/or presenting to a user waveforms like physiological signal 312.

Figure 4A:
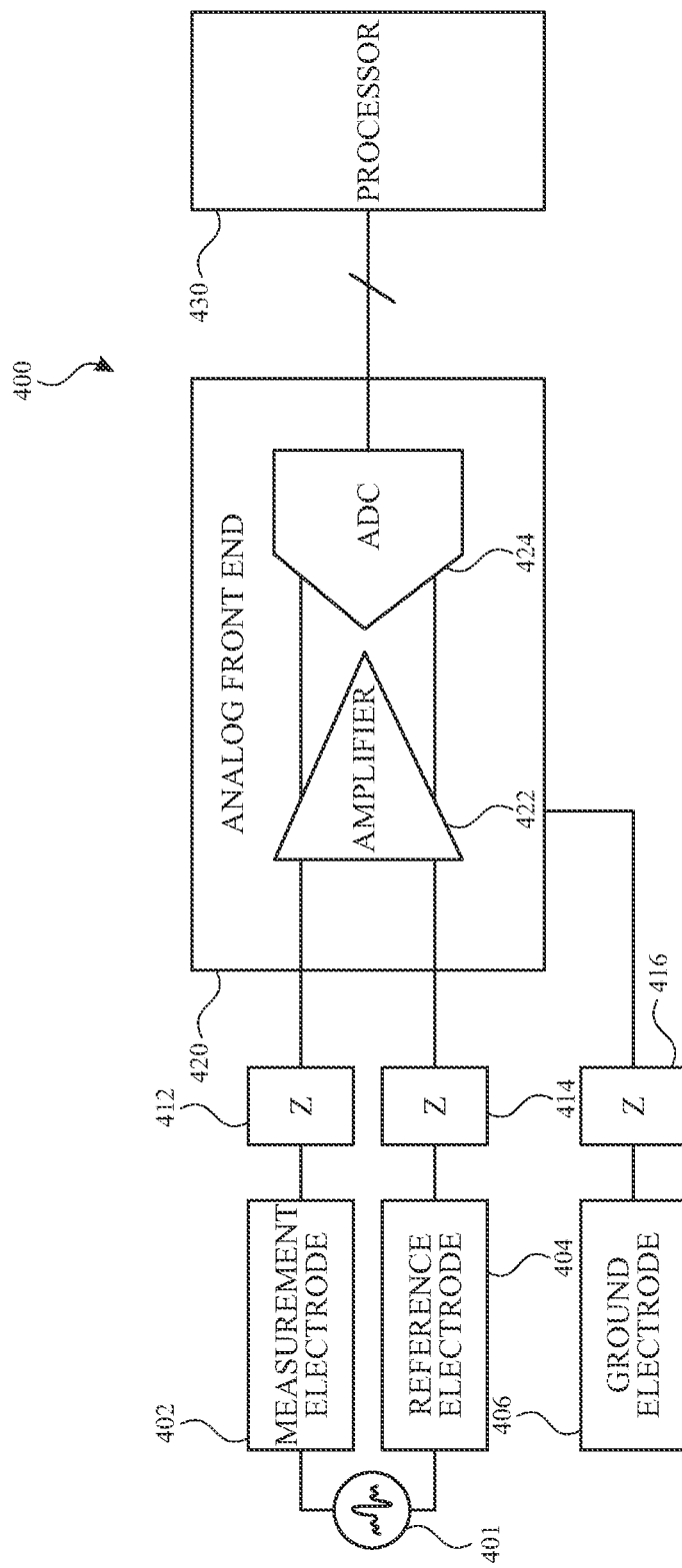
FIGS. 4A-4B illustrate example systems for measuring physiological signals according to examples of the disclosure.
Figure 4B:
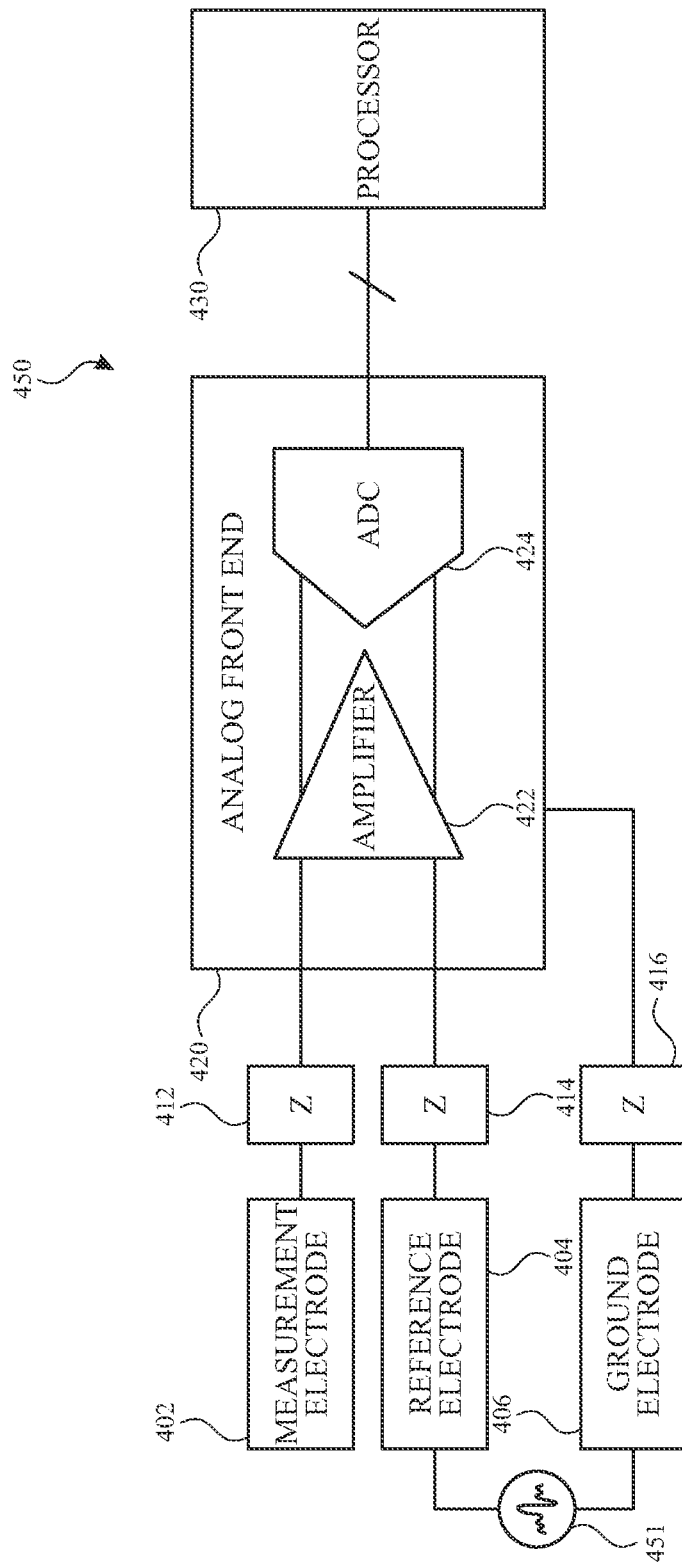

FIGS. 4A-4B illustrate example systems for measuring physiological signals according to examples of the disclosure. In FIG. 4A, circuit 400 can include processor 430 (e.g., corresponding to DSP 206 and/or host processor 208), analog front end 420, measurement electrode 402 (e.g., corresponding to measurement electrode 166C), reference electrode 404, and ground electrode 406 (e.g., corresponding to reference electrode 166A and reference electrode 166B). In some examples, circuit 400 resides on a mobile device (e.g., a wearable device 150). In some examples, analog front end 420 includes amplifier 422 and analog-to-digital converter (ADC) 424. Amplifier 422 can be a differential amplifier coupled to measurement electrode 402 (e.g., on the inverting input or on the non-inverting input) and to reference electrode 404 (e.g., on the non-inverting input or on the inverting input). In some examples, ground electrode 406 can be coupled to analog front end 420 to provide a shared ground reference between circuit 400 and ground electrode 406 (e.g., ground electrode 406 can provide a system ground reference voltage). In some examples, circuit 400 can include networks 412, 414, and 416, along the signal paths for the measurement electrode 402, reference electrode 404, and ground electrode 406, respectively. In some examples, networks 412, 414, and 416 can include circuit components (e.g., resistors, capacitors, inductors and/or diodes) and/or can include impedances inherent in circuit 400 (e.g., routing impedances, parasitic impedances, etc.). In some examples, networks 412, 414 and 416 can provide electrostatic discharge (ESD) protection for the circuit 400 and/or provide safety by limiting or preventing electrical currents being applied to the user's skin and/or preventing unexpected or unintentional external signals from entering the device and causing damage. In some examples, amplifier 422 can output an amplified differential signal and analog-to-digital converter 424 can convert the amplified differential signal into a digital signal. In some examples, amplifier 422 can output an amplified single-ended output. In some examples, the output of analog-to-digital converter 424 can be a multi-bit signal (e.g., 8 bits, 12 bits, 24 bits, etc.) coupled to processor 430. The multi-bit signal can be transmitted from analog front end 420 to processor 430 serially or in parallel. In some examples, analog-to-digital converter 424 can be a differential analog-to-digital converter and convert a differential analog input to a digital output. In some examples, analog-to-digital converter 424 can be single-ended and convert a single-ended analog input to a digital output. In some examples, differential amplifier 422 can be implemented with two single-ended amplifiers and ADC 424 can be implemented with two ADCs (each connected to the output of one of the single-ended amplifiers).

In some examples, a user can wear the wearable device including circuit 400. In such examples, reference electrode 404 and ground electrode 406 can contact with the wrist of the user. When a user touches measurement electrode 402 (e.g., electrode 166C on crown 162 of wearable device 150), measurement electrode 402 can receive a physiological signal from the user. In FIG. 4A, the user is represented as physiological signal source 401. In some examples, when the user touches measurement electrode 402, a path can be created through physiological signal source 401 from measurement electrode 402 and reference electrode 404 and/or ground electrode 406 (e.g., from the user's finger across the user's chest to the wrist upon which the user is wearing the wearable device and to reference electrode 404 and/or ground electrode 406). In some examples, contacting measurement electrode 402 can cause circuit 400 to measure a physiological signal (e.g., as illustrated in and described with respect to FIG. 3A) from physiological signal source 401.

FIG. 4B illustrates an example circuit diagram in which a user of the device contacts the housing of the wearable device instead of a measurement electrode. In FIG. 4B, circuit 450 can include the same components as circuit 400, the description of which is omitted for brevity. In some examples, when the user touches the housing of the wearable device, an alternative path can be created through physiological signal source 451 from reference electrode 404 (e.g., electrode 166A connected to the user's wrist) and ground electrode 406 (e.g., the housing of the wearable device can be grounded to system ground via ground electrode 406). In some examples, the alternative path can cause physiological signal source 451 to inject a physiological signal between reference electrode 404 and ground electrode 406. In some examples, the physiological signal can cause amplifier 422 to detect and amplify a physiological signal. In such examples, processor 430 may misinterpret the signal from the physiological sensor(s) as a proper physiological signal. However, as described above with respect to FIG. 3B, the resulting physiological signal can be attenuated, unstable, or otherwise unreliable.

Figure 5A:
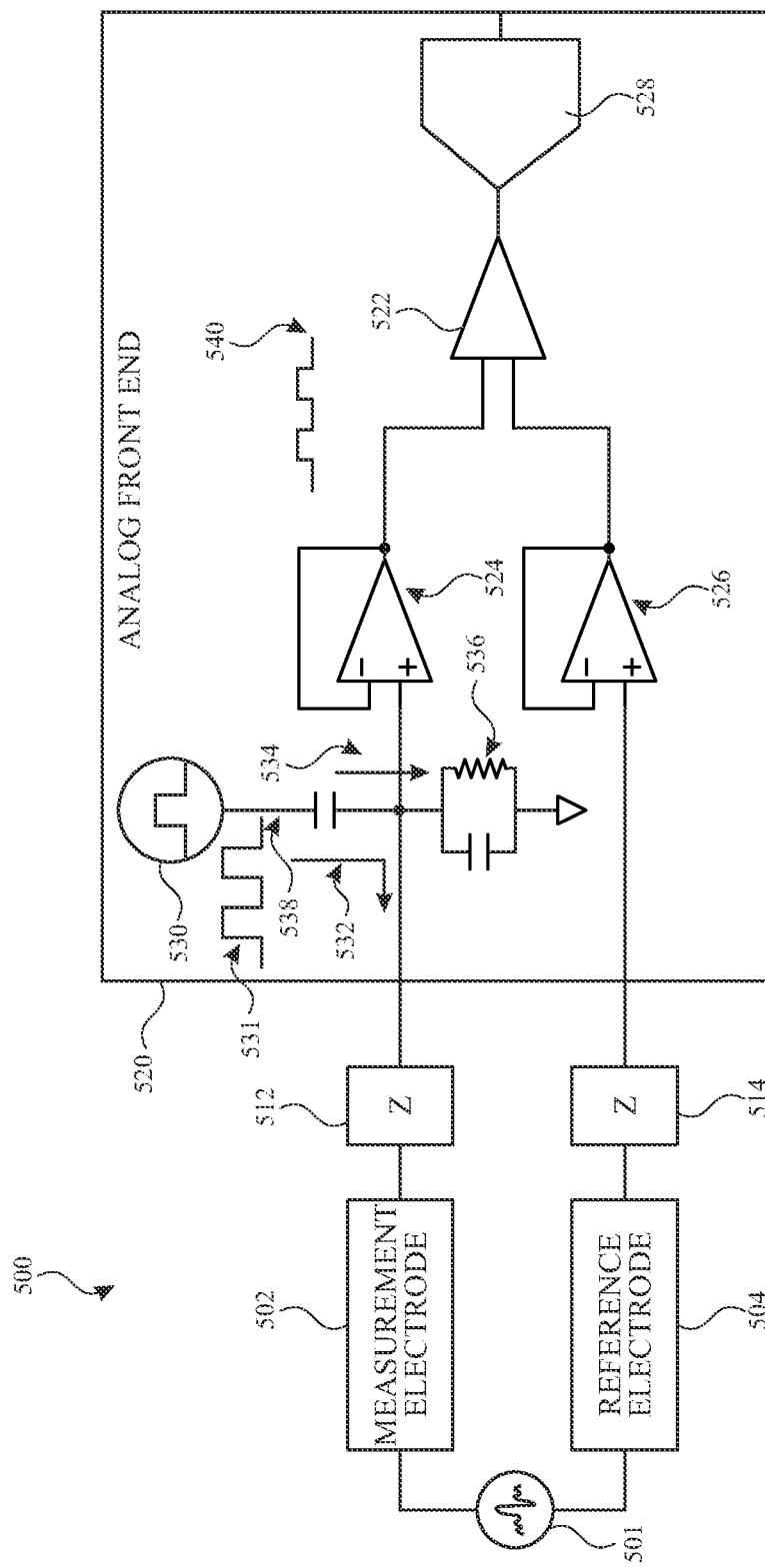
FIGS. 5A-5B illustrate example systems for measuring physiological signals and for contact detection according to examples of the disclosure.
Figure 5B:
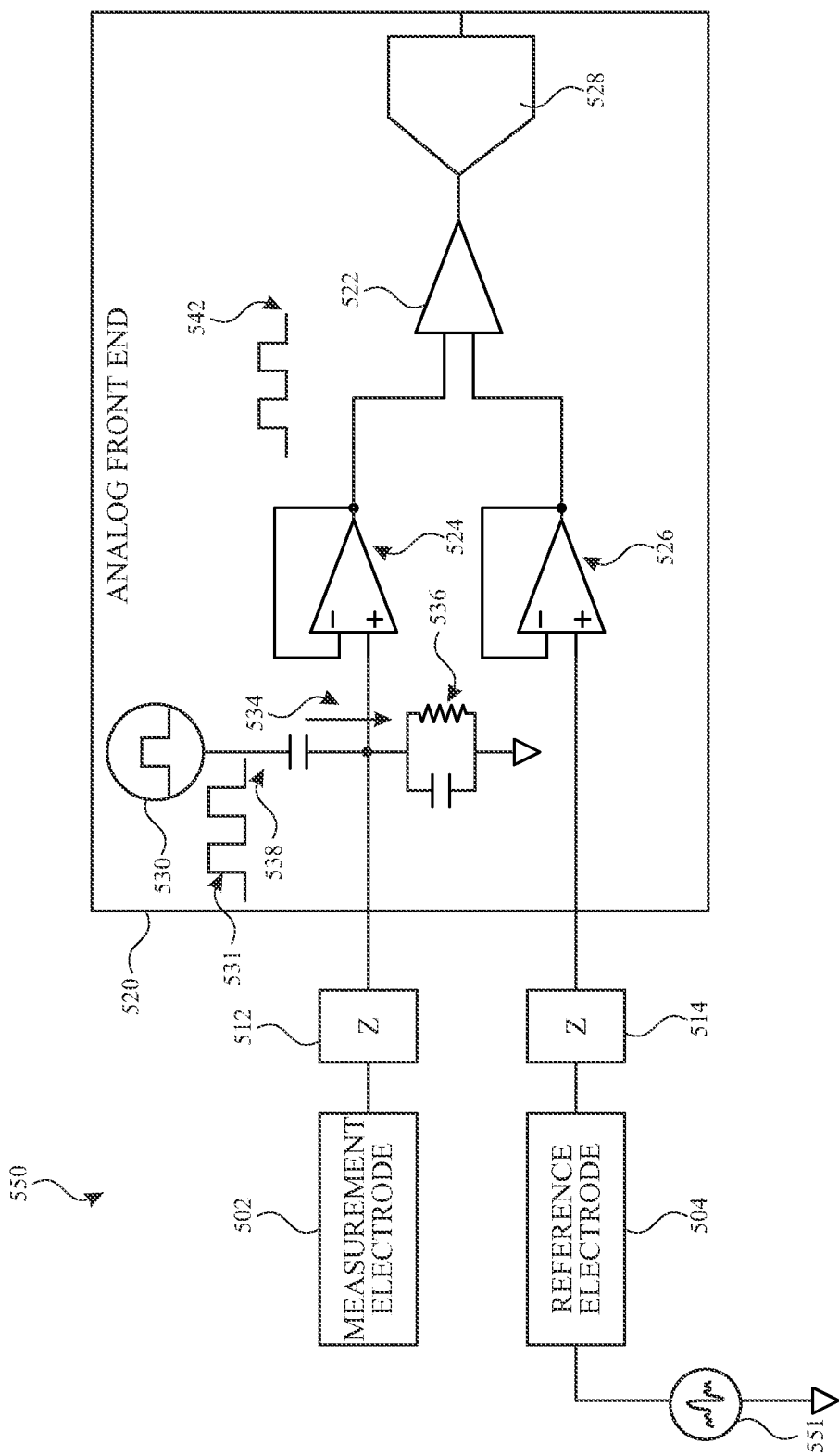

FIGS. 5A-5B illustrate example systems for measuring physiological signals and for contact detection according to examples of the disclosure. For ease of description, FIGS. 5A-5B focus on a measurement electrode, a reference electrode and the analog circuitry for measuring physiological signals and for contact detection; processing circuitry, and a ground reference electrode are not illustrated. In FIG. 5A, circuit 500 can include analog front end 520, measurement electrode 502 (e.g., corresponding to measurement electrode 166C) and reference electrode 504 (e.g., corresponding to reference electrode 166A and/or reference electrode 166B). Analog front end 520 can include amplifier 522 (e.g., similar to amplifier 422), analog-to-digital converter 528 (e.g., similar to ADC 424), buffers 524 and 526, and test signal circuitry. In some examples, buffers 524 and 526 can provide an impedance matching interface for the electrodes (e.g., matching the impedance of the user's body contacting with the respective electrode). In some examples, buffer 524 and 526 can be designed to accommodate the large input impedances 512, 514 between the electrodes and the buffer 524 and 526. In some examples, buffer 524 and 526 can be designed to reduce noise or interference from the input networks that may enter inputs to amplifier 522.

In some examples, the test signal circuitry (e.g., stimulation circuit) can include test signal generator 530 and capacitor 538. In some examples, test signal generator 530 can be a square wave generator, a clock generator, a periodic signal generator or other suitable signal generator. In some examples, test signal generator can include a digital to analog converter (DAC) to convert a digital signal into an analog stimulation signal. Test signal 531 (e.g., stimulation signal) generated by test signal generator 530 can be a square wave, a sine wave, a trapezoidal wave, a saw-tooth wave or any other suitable periodically oscillating, non-oscillating or non-periodic (e.g., pseudo-noise signal) waveform. The test signal, regardless of waveform, can be known or predetermined to the system to enable detection of the resulting measured test signal, in some examples as described herein. Test signal 531 can be capacitively coupled via capacitor 538 to measurement electrode 502. In some examples, test signal generator 530 can be controlled by a processor (e.g., DSP 206, host processor 208, processor 430). In some examples, the processor can change the frequency and/or amplitude of test signal 531 and/or enable and disable test signal generator 530. In some examples, the test signal generator 530 can be a clock output of processor 430.

In some examples, analog front end 520 can include an impedance network 536. In some examples, impedance network 536 can be one or more discrete capacitors and/or one or more discrete resistors. In some examples, impedance network 536 can represent parasitic impedances in the system. In some examples, impedance network 536 can be one or more capacitors (including respective parasitic impedances). In some examples, capacitor 538 and impedance network 536 form a voltage divider through path 534 to ground and test signal 531 generated by test signal generator 530 can be divided by the voltage divider. Buffer 524 can measure a node between capacitor 538 and impedance network 536. The resulting measured test signal can be used to detect contact on measurement electrode 502.

In some examples, the amplitude (e.g., voltage level) of the measured test signal can depend on the load experienced by the test signal. For example, when a user touches measurement electrode 502, the resulting measured test signal can be attenuated. As illustrated in FIG. 5A, contact between a user (e.g., a finger) and measurement electrode 502 can form a path 532 for test signal 531. In some examples, path 532 can be formed through physiological signal source 501 (e.g., the body of the user) to system ground via the ground electrode (e.g., ground electrode 406 contacting the user's wrist). In some examples, a user can be contacting measurement electrode 502 with a first finger (e.g., an index finger) and the housing of the device with a second finger (e.g., a thumb). In such cases, path 532 for test signal 531 can be formed through physiological signal source 501 (e.g., the body of the user) to system ground through the finger touching the housing of the device (e.g., the housing of the device can be grounded to system ground). Thus, path 532 can form an impedance in parallel to path 534 (through impedance network 536) and change the loading experienced by test signal 531. In such examples, the resulting measured test signal 540 at buffer 524 can be attenuated. In contrast, when a user is not touching measurement electrode 502 (or is contacting the housing), the resulting measured test signal may not be attenuated (or may be attenuated less). As illustrated in FIG. 5B, without contact on measurement electrode 502, path 532 may not be formed to system ground. Without path 532 to system ground for test signal 540, the resulting measured test signal 542 may not be attenuated (or may be attenuated less) than expected from the voltage divider of capacitor 538 and impedance network 536. Comparing the amplitude of resulting measured test signals 540 and 542, measured test signal 540 corresponding to contact on measurement electrode 502 can be more attenuated than measured test signal 542. In some examples, test signal 531 can travel through path 532, through physiological signal source 501, and into reference electrode 504 and can be detected by buffer 526. In some examples, detection of the resulting test signal by buffer 526 can be sufficient to determine that a user is contacting with measurement electrode 502. In some examples, a differential measurement can be performed on the resulting signal detected by buffer 526 and the resulting signal detected by buffer 524 to determine the amplitude level of the resulting test signal. In some examples, a single-ended measurement can be performed to determine the amplitude of the resulting test signal (e.g., without using reference electrode 504 and buffer 526).

In some examples, the response of test signal 531 to the load can depend on the frequency of test signal 531 and the respective impedance of the signal paths. In some examples, the frequency of test signal 531 can be varied to determine the load of the signal paths at the respective frequency (e.g., the quality of the skin-to-electrode connection as a function of the test signal frequency can be determined). In some examples, an initialization process can be used to select a frequency for differentiating between when measurement electrode 502 is contacted and when it is not contacted (e.g., a frequency for test signal 531 that results in an observable change in resulting test signal amplitude). In some examples, test signal 531 can include a plurality of frequencies concurrently (e.g., test signal 531 can include multiple frequency components). In such an example, the reactance of the system to different frequencies can be determined at one time.

A threshold amplitude (e.g., voltage level) can be used to determine whether measurement electrode 502 is contacted. When the measured test signal is less than a threshold amplitude, the system (e.g., DSP 206, host processor 208, processor 430) can determine that the measurement electrode is contacted (e.g., sufficient skin-to-electrode coupling exists for high-quality physiological measurements). When the measured test signal is greater than or equal to the threshold amplitude, the system can determine that the measurement electrode is not contacted (or that the housing is contacted, or that there is insufficient skin-to-electrode coupling for a high-quality physiological measurement). The threshold amplitude can be set, for example, based on empirical study of expected range of load impedance from skin-to-electrode coupling. Additionally, the threshold amplitude can be set based on other factors including accuracy of the resulting waveform and the desired sensitivity (e.g., with respect false positives). As described herein, detecting contact with the measurement electrode can be used to differentiate between a reliable measured physiological signal (e.g., such as physiological signal 302) from an unreliable measured physiological signal. In some examples, the system can provide a notification for the user to contact the measurement electrode to begin measuring a physiological signal. In some examples, as described herein, contact detection can be used as a trigger to begin physiological signal measurements and/or as a trigger to end physiological signal measurements. In some examples, contact detection can be used to assign a confidence to physiological signal during a measurement session. In some examples, beginning physiological signal measurements can include acquiring the physiological signal (e.g., by data buffer 204 and/or DSP 206), storing the physiological signal (e.g., in program storage 210) and/or displaying the physiological signal on the display. In some examples, when the system determines that the measurement electrode is not contacted, the system can forego measuring the physiological signal (e.g., powering down the circuit, discarding the physiological signal measurements, or otherwise not process incoming signals). In some examples, when the system determines that the measurement electrode is not contacted, the system can still measure the physiological signal, but with a low confidence value indicative that the physiological signal is low-quality (e.g., may not be reliable for one or more intended uses). In some examples, the low confidence can be represented in a binary manner (e.g., a low-confidence/low-quality flag can be set. In some examples, the confidence can be represented in another manner (e.g., a probability) representative of the quality. In some examples, when the confidence is below a threshold or when the low-confidence/low-quality flag is set, a notification can be presented to the user to indicate that the measured physiological signal measurement may be unreliable or low quality (e.g., display the physiological signal with a visual indicator, display a notification on the display of the device and/or any other visual feedback, and/or an audio feedback and/or a haptic feedback and/or any other suitable feedback mechanism).

In some examples, when a user contacts measurement electrode 502, a physiological signal from physiological signal source 501 can enter circuit 500. In some examples, the physiological signal can be mixed or otherwise added to test signal 531 generated by test signal generator 530. In some examples, the frequency of test signal 531 can be higher than the frequency of physiological signal. For example, the frequency spectrum of a physiological signal can be between 0.5 Hz to 40 Hz and the frequency of test signal 531 can be 100 Hz, 135 Hz, 200 Hz, 250 Hz, 400 Hz, 500 Hz, 600 Hz, or any other suitable frequency above 40 Hz. In some examples, the frequency spectrum of a physiological signal can be between 0 Hz to 150 Hz and the frequency of test signal 531 can be 500 Hz, 600 Hz, or any other suitable frequency above 150 Hz. In some examples, the amplitude of test signal 531 can be smaller than the amplitude of the physiological signal. In such examples, the physiological signal can act as a carrier wave for test signal 531 (e.g., in a manner similar to amplitude modulation). In some embodiments, a filter (e.g., a high-pass filter or a band-pass filter) can be used to filter the physiological signal and leave the test signal (e.g., test signal 540) to be compared against the threshold to determine whether measurement electrode 502 is contacted.

In some examples, after contact with measurement electrode 502 is determined, test signal generator 530 can stop generating test signal 531. In such examples, stopping test signal generation can save power and/or reduce or eliminate the need for filtering (of the test signal from the physiological signal). In some examples, even after contact with measurement electrode 502 is determined, test signal generator 530 continues providing test signal 531. In such examples, a filter (e.g., a low-pass filter or band-pass filter) can be used to filter test signal 531 and leave the physiological signal for measurement and/or processing. In some examples, continuing to generate test signal 531 can allow the system (e.g., DSP 206, host processor 208, processor 430) to continue to determine that the user is contacting measurement electrode 502. In some examples, when the user of the device stops contact with measurement electrode 502, the system can determine that contact has stopped and cease measuring and/or processing the physiological signal. In some examples, the system can provide a notification to the user regarding the termination of contact with the measurement electrode during a physiological signal measurement session. In some examples, test signal generation can be periodically restarted to determine whether measurement electrode 502 is contacted. In some examples, contact detection can be continuous (e.g., the test signal can be generated at all times), periodic (e.g., generated once a second, once a minute, once an hour), or may be generated in response to a trigger (e.g., launching a physiological signal application, beginning a physiological signal measurement session, while a wearable device is determined to be worn, etc.).

Figure 12:
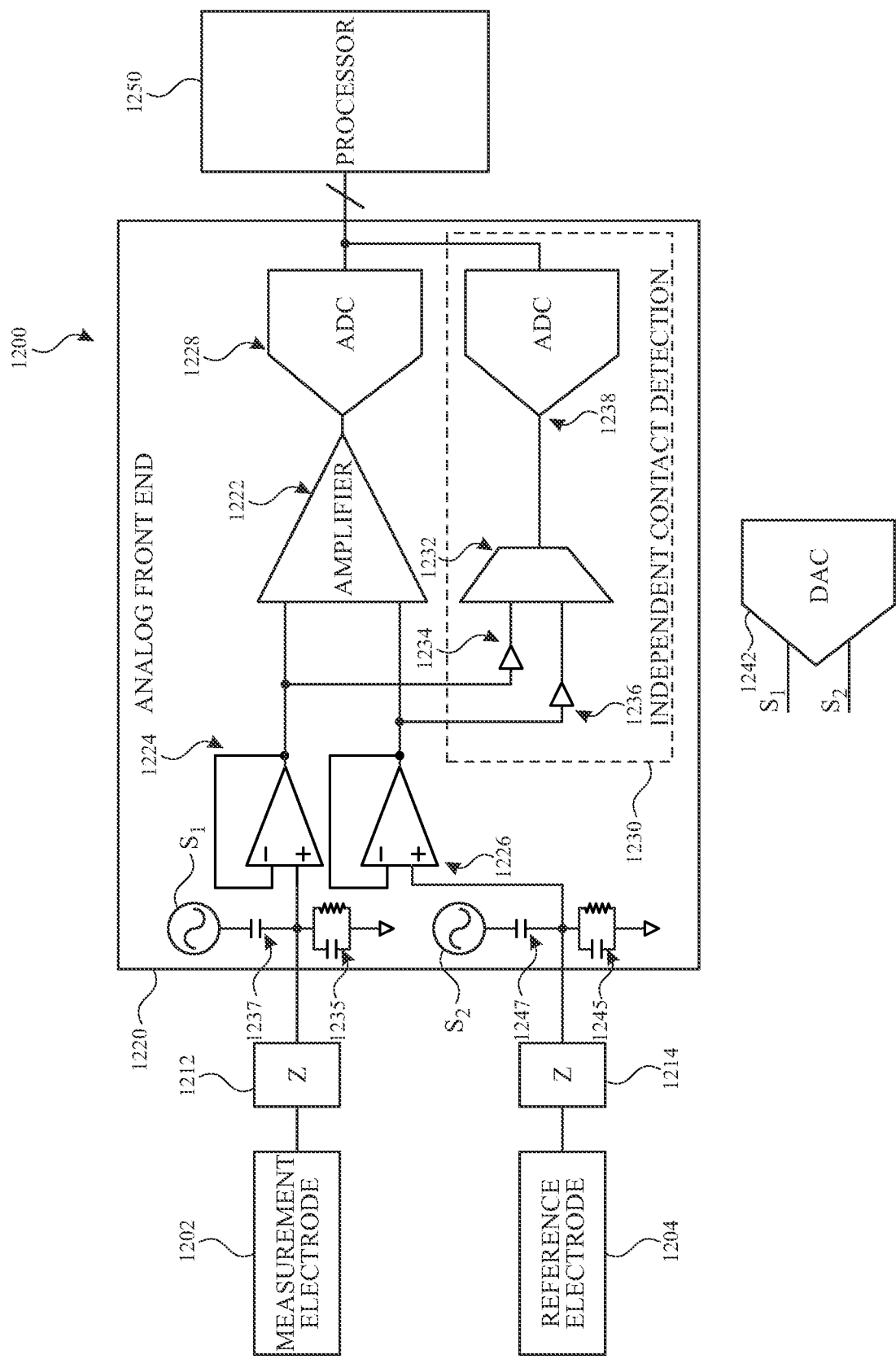
FIG. 12 illustrates an example system for measuring physiological signals and for contact detection on multiple electrodes according to examples of the disclosure.

Although FIGS. 5A-5B illustrate the integration of the test signal circuitry with the physiological signal measurement circuitry, it is understood that test signal circuitry can be implemented in a different manner. For example, the test signal circuitry can include an amplifier or other front end circuitry (e.g., separate from amplifier 524, amplifier 522, etc.) to perform the functions of measuring the test signal and performing contact detection. In some examples (e.g., as illustrated in FIG. 12), separate signal paths can be used for contact detection and physiological sensing (e.g., not integrating the test signal circuitry with the physiological signal measurement circuitry). In some examples, implementing contact detection and physiological sensing separately can allow for optimization of the circuitry for contact detection for the frequencies, signal range and/or signal precision of the test signal for contact detection and optimization of the circuitry for the frequencies, signal range and/or signal precision for physiological sensing. In some examples a switching circuit can be provided to couple the test signal circuitry (e.g., test signal generator and measurement amplifier) to the measurement electrode during contact detection and to decouple the measurement electrode from the test signal circuitry during the physiological signal measurement. In some examples, the test signal circuitry can be integrated with saturation detection circuitry, as will be described below. Additionally, although illustrated as a discrete source in FIG. 5A-5B, test signal 531 can be generated by a processor (e.g., DSP 206, host processor 208). In some examples, the same processor can also be coupled to receive the measured test signals from the output of buffer 524 or another buffer or amplifier circuit.

Furthermore, although FIGS. 5A-5B illustrate the integration of the test signal circuitry onto the signal path of measurement electrode 502, it is understood that similar test signal circuitry can be integrated onto the signal path of reference electrode 504 to detect contact between the user (e.g., wrist) and reference electrode 504 in a similar manner (e.g., as illustrated in FIG. 12). Additionally, although FIGS. 5A-5B illustrate one measurement electrode 502 and one reference electrode 504, in some examples, the system can have a plurality of measurement electrodes and/or a plurality of reference electrodes, and similar test signal circuitry can be integrated with some or all of these electrodes.

Figure 6:
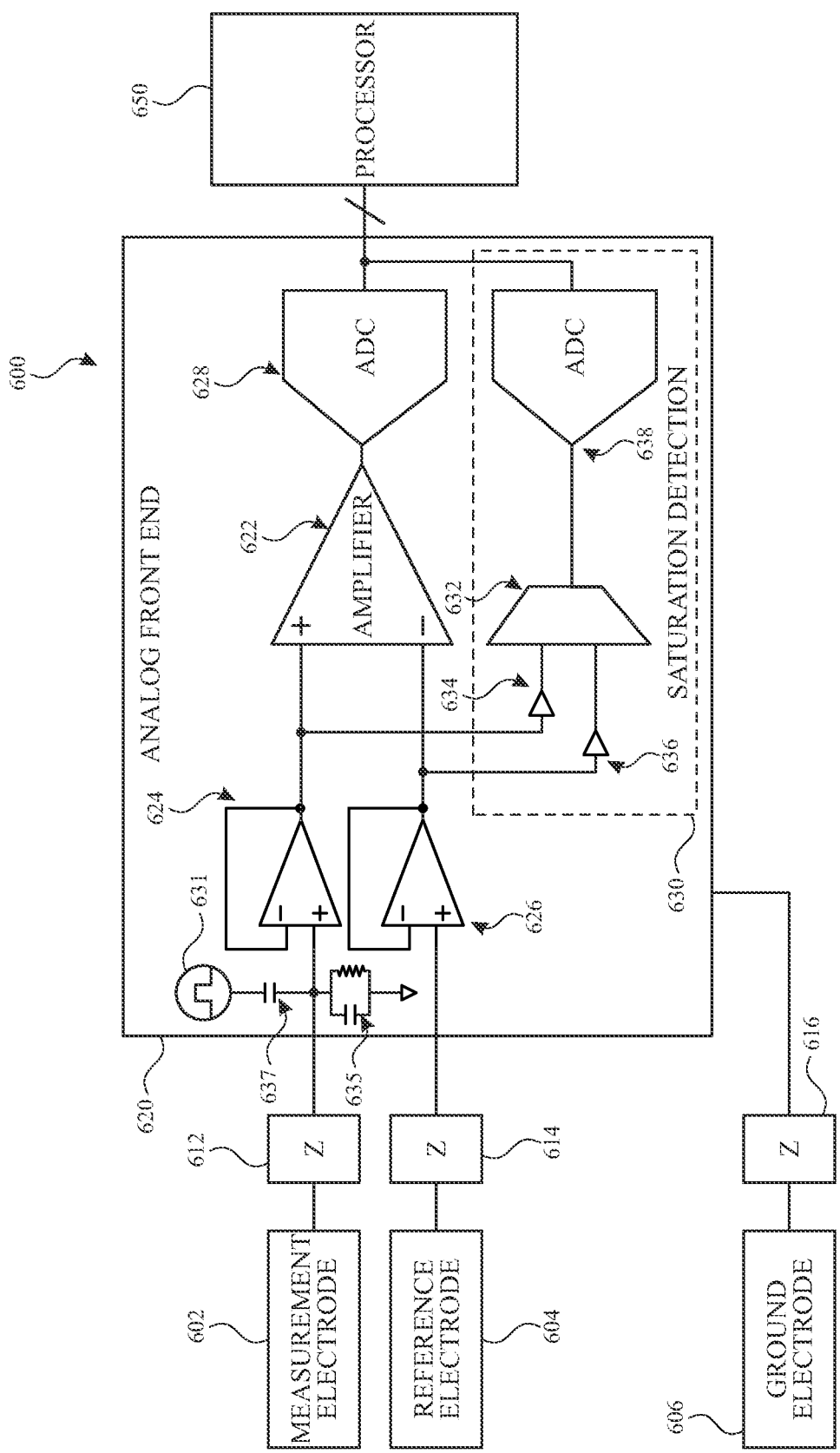
FIG. 6 illustrates an example system for measuring physiological signals according to examples of the disclosure.

FIG. 6 illustrates an example system for measuring physiological signals (and for contact detection and/or saturation detection) according to examples of the disclosure. In some examples, circuit 600 can be similar to circuit 500 (including impedance networks 612 and 614 corresponding to impedance networks 512 and 514, amplifier 622 corresponding to amplifier 522, ADC 628 corresponding to ADC 528, buffers 624 and 626 corresponding to buffers 524 and 526, and test signal circuitry including test signal generator 631 and capacitor 637 corresponding to test signal generator 530 and capacitor 538, and impedance network 635 corresponding to impedance network 536), but analog front end 620 includes saturation detection circuit 630. In some examples, saturation detection circuit 630 includes buffers 634 and 636, multiplexer 632, and analog-to-digital converter 638. In some examples, buffers 634 and 636 are coupled to route signals from measurement electrode 602 and reference electrode 604, respectively, to multiplexer 632. In some examples, multiplexer 632 multiplexes between selecting the signal from measurement electrode 602 to pass through to processor 650 and selecting the signal from reference electrode 604 to pass through to processor 650. In some examples, processor 650 can control the multiplexing of multiplexer 632. In some examples, analog-to-digital converter 638 converts the analog signal from multiplexer 632 to a digital signal. In some examples, the digital signal is then input to processor 650. In some examples, the digital output of analog-to-digital converter 638 can be a multi-bit signal (e.g., 4 bits, 6 bits, 8 bits, 10 bits, 12 bits, etc.). In some examples, the digital output of analog-to-digital converter 638 can have fewer bits than analog-to-digital converter 628, as the precision of the measurement for saturation may be less for saturation detection than for measuring the physiological signal. In some examples, rather than time-multiplexing the measurement of signals for saturation detection, multiplexer 632 can be omitted and each of buffers 634 and 636 can be coupled to its own ADC (not shown). In some examples, saturation detection circuit 630 can measure the signal from measurement electrode 602 and reference electrode 604 to determine (e.g., at processor 650) whether the corresponding measurement circuitry has saturated. For example, the incoming signal (e.g., a physiological signal from a user, or other non-physiological signals) can have an amplitude beyond the supported dynamic range of the electrode or buffers. In some examples, if the incoming signal has saturated the measurement circuitry (e.g., buffers 624 and/or 626), the resulting signal can be distorted (e.g., clipped) or otherwise transformed, and likely unusable for reliable measurement. When one or both inputs are saturated, the device can forego measuring the physiological signal (e.g., power down some or all of the circuit, such as amplifier 622, ADC 628, etc.) or otherwise not process or store the incoming signal.

As described above, in some examples, saturation detection circuit 630 can be used for contact detection (e.g., as described with reference to FIG. 12 using similar circuitry as shown in saturation detection circuit 630 for contact detection). For example, while the test signal is applied by test signal circuitry, the resulting signal can be measured by buffer 634 in saturation detection circuit 630, can be converted into a digital signal by ADC 638 and transmitted to processor 650 for contact determination based on attenuation of the measured test signal.

Figure 7:
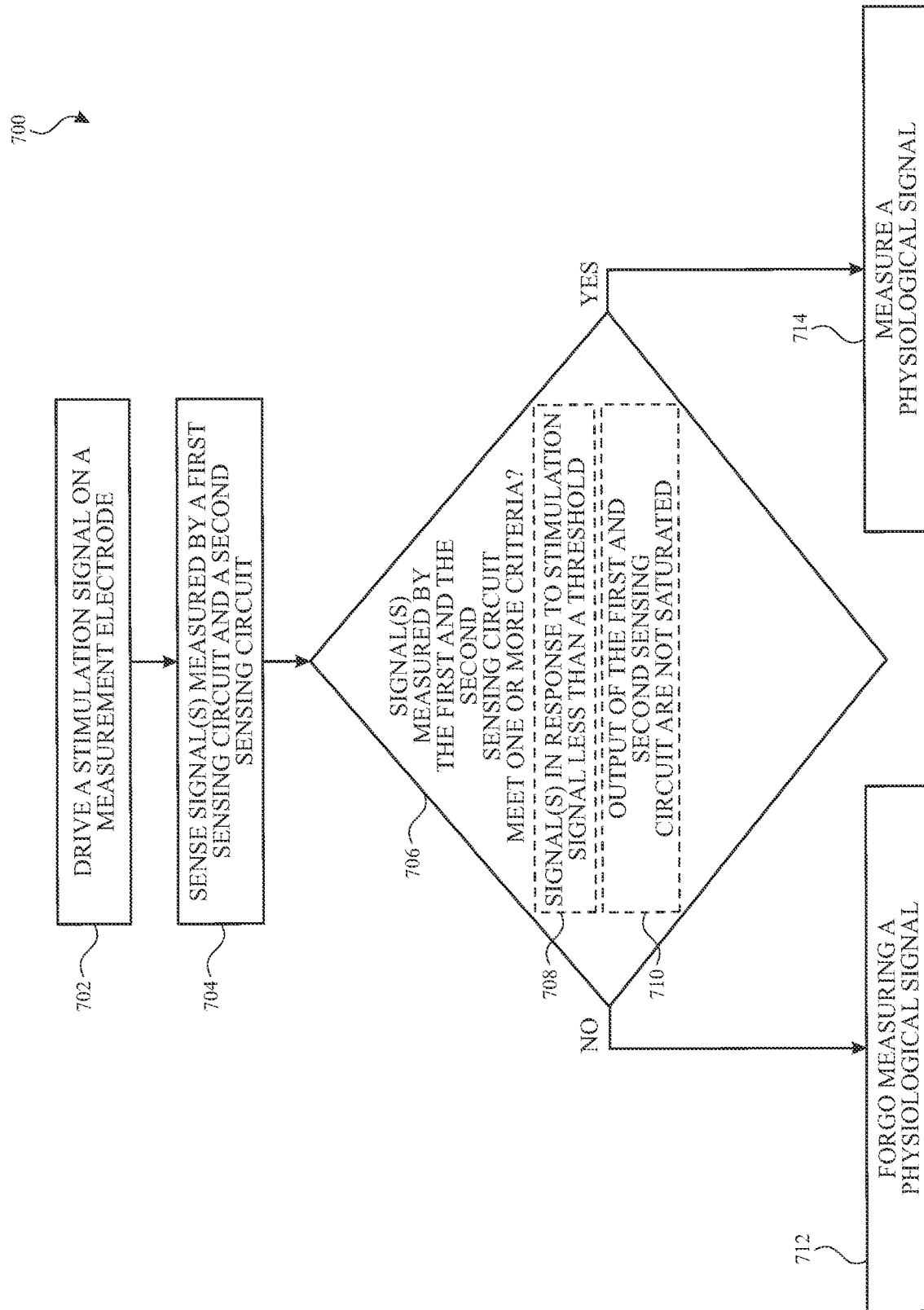
FIG. 7 illustrates an exemplary process of physiological signal detection including contact detection and/or saturation detection according to examples of the disclosure.

FIG. 7 illustrates an exemplary process 700 of physiological signal detection including contact detection and/or saturation detection according to examples of the disclosure. Process 700 can be performed by one or more processors of the system (e.g., DSP 206, host processor 208, processor 650, etc.) programmed to perform process 700. At 702, a stimulation signal can be driven on a measurement electrode. In some examples, the stimulation signal (e.g., test signal 531) can be driven by a stimulation circuit (e.g., test signal circuit) that is coupled to a measurement electrode (e.g., similar to the test signal circuitry described with respect to FIGS. 5A-5B). At 704, the system can sense one or more signals measured by a first sensing circuit and a second sensing circuit (e.g., corresponding to amplifier/buffer 524 and 526). In some examples, the first sensing circuit can receive the one or more signals from a measurement electrode and/or a stimulation circuit and can include a buffer (e.g., corresponding to amplifier/buffer 524). In some examples, the one or more signals measured by the first sensing circuit include a physiological signal injected via a user contact with the measurement electrode. In some examples, the one or more signals measured by the first sense circuit can include a signal measured in response to the stimulation signal (e.g., the resulting test signals 540 or 542). In some examples, the second sensing circuit can receive the one or more signals from a reference electrode and can include a buffer (e.g., corresponding to amplifier/buffer 526). In some examples, the one or more signals measured by a second sense circuit can represent a reference voltage level of a user's body. In some examples, depending on the physiology and the impedance of the user, the one or more signals measured by a second sense circuit can include a physiological signal injected via a user contact with the measurement electrode (e.g., thus closing a circuit loop between the measurement electrode and the reference electrode, as described with respect to FIGS. 4A-5B).

At 706, in accordance with the one or more signals measured by the first and second sensing circuit meeting one or more criteria (e.g., as determined by processor 650), the system can measure a physiological signal at 714, or in accordance with the one or more signals measured by the first and second sensing circuit not meeting one of more criteria (e.g., as determined by processor 650), the system can forgo measuring a physiological signal at 712. As described above with respect to FIGS. 5A-5B, measuring the physiological signal can include acquiring the physiological signal (e.g., by data buffer 204 and/or DSP 206), storing the physiological signal (e.g., in program storage 210) and/or displaying the physiological signal on the display (e.g., touch screen 212). In some examples, forgoing measuring a physiological signal can include powering down the circuitry, discarding any stored signal measurements, or otherwise not processing incoming signals. In some examples, the system can provide a notification for the user of the device to contact with the measurement electrode to begin measurement of the physiological signal. In some examples, the notification can be a notification displayed on the display of the device and/or any other visual feedback, and/or an audio feedback and/or a haptic feedback and/or any other suitable feedback mechanism. In some examples, the system can wait for a threshold amount of time for the signals to meeting the one or more criteria (e.g., wait for the user to contact the measurement electrode and/or wait for the signals to no longer be saturated). In some examples, after a timeout threshold, the system can forgo measuring the physiological signal.

In some examples, the one or more criteria optionally includes (708) a criterion that requires (e.g., that is satisfied when) a signal of the one or more signals detected in response to the stimulation signal (e.g., the measured test signal) is less than a threshold. For example, contact with the measurement electrode can be indicated by the resulting measured test signal measured in response to driving the stimulation signal being below a threshold value (corresponding to resulting measured test signal 540). While the user is contacting the measurement electrode, the system can measure the physiological signal that is introduced into the system (as another of the one or more signals) via the user's contact with the measurement electrode. When the resulting measured test signal is not below a threshold value (corresponding to resulting measured test signal 542), the system can forgo measuring a physiological signal (as described above with respect to FIGS. 5A-5B).

In some examples, the one or more criteria optionally includes (710) a criterion that requires (e.g., that is satisfied when) the output of the first sensing circuit and the output of the second sensing circuit are not saturated. In some examples, a saturation detection circuit can include circuitry (e.g., saturation detection circuit 630) coupled to the output of the first sensing circuit and the output of the second sensing circuit. In some examples, the saturation detection circuit can include buffers (e.g., buffers 634, 636), a multiplexer (e.g., multiplexer 632) and an analog-to-digital converter (e.g., ADC 638) to convert the signals from the buffers to a digital signal. In some examples, the saturation detection circuit and processor 650 can determine whether the outputs of the first sensing circuit and/or the second sensing circuit are saturated. For example, when the measured voltage is at the power supply voltage of the first/second sensing circuit for a threshold period of time, the first/second sensing circuit can be determined by processor 650 to be saturated. Otherwise the first/second sensing circuit can be determined to be non-saturated. In some examples, whether the first or second sensing circuit is saturation can be determined based on other characteristics (e.g., the morphology of the measured signal). In some examples, when the outputs of the first and second sensing circuit are both not saturated, then the system can measure the physiological signal. In some examples, when the outputs of one or both of the first sensing circuit and second sensing circuit are saturated, then the system can forgo measuring the physiological signal. In some examples, the one or more criteria can include both criteria 708 and 710, can include only one criterion, or can include criteria other than criteria 708 and 710. In some examples, the contact and/or saturation detection can be performed continuously to indicate the quality of a physiological signal measurement during physiological signal measurement. In some examples, the contact and/or saturation detection can be used to terminate a physiological signal measurement session. In some examples, the contact and/or saturation detection can be performed and the results can be used to trigger a physiological signal measurement session.

Figure 8:
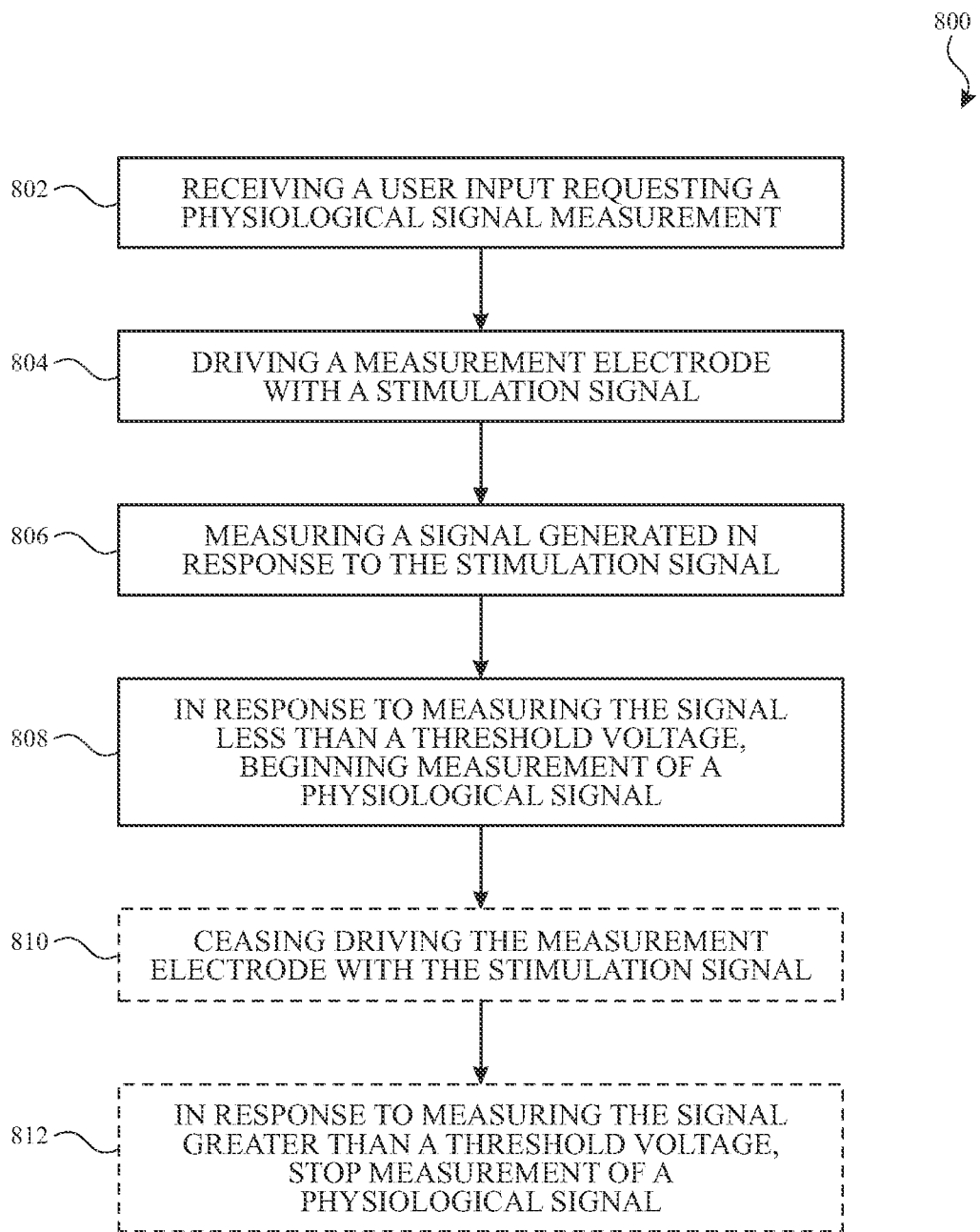
FIG. 8 illustrates an exemplary process of physiological signal detection including contact detection and/or saturation detection according to examples of the disclosure.

FIG. 8 illustrates an exemplary process 800 of physiological signal detection including contact detection and/or saturation detection according to examples of the disclosure. Process 800 can be performed by one or more processors of the system (e.g., DSP 206, host processor 208, processor 650, etc.) programmed to perform process 800. At 802, the system can receive a user input requesting a physiological signal measurement. In some examples, the user input can be a user opening an application for measuring or viewing a physiological signal. In some examples, the user input can be a request to begin a physiological signal measurement session. A session can be a predefined period of time (e.g., 10 seconds, 30 seconds, 1 minute, etc.), during which the physiological signal can be measured. The session can begin with the user input and end at the conclusion of the duration. In some examples, the measured physiological signal measured during the session can be analyzed, categorized, stored and/or displayed. At 804, in response to the user request, the system can drive a measurement electrode (e.g., corresponding to measurement electrode 166C, measurement electrode 402, measurement electrode 502) with a stimulation signal (similar to the discussion of 702 above). In some examples, in response to the user request, the system can power up the physiological measurement circuitry. At 806, the system can measure a signal generated in response to the stimulation signal. In some examples, the signal can be a resulting test signal (e.g., resulting stimulation signal) that can be measured by sense circuitry. In some examples, the sense circuitry can be a buffer coupled to a stimulation circuit and the measurement electrode (e.g., buffer 524). In some examples, the resulting test signal can be measured from the output of a differential amplifier (e.g., differential amplifier 522). In some examples, the signal generated in response to the stimulation signal (e.g., resulting test signal) can be a divided (e.g., by a voltage divider described with respect to FIGS. 5A-5B) version of the stimulation signal and/or can be filtered (e.g., high pass or band-pass filtered) to exclude physiological signal measurements on the measurement electrode. At 808, in response to measuring that the signal (e.g., resulting test signal) is less than a threshold voltage (e.g., as determined by a processor, such as processor 650), the system can begin measurement of a physiological signal. In some examples, the signal can be less than a threshold voltage when a user is contacting the measurement electrode. In some examples, beginning measuring the physiological signal can include acquiring the physiological signal (e.g., by data buffer 204 and/or DSP 206), storing the physiological signal (e.g., in program storage 210) and/or displaying the physiological signal on the display. In some examples, the physiological signal can be acquired from the measurement electrode via the sense circuitry (e.g., analog front end 420, 520). In some examples, the physiological signal measurement can be a differential measurement between a measurement electrode and a reference electrode. For example, a differential amplifier (e.g., 422, 522) can output a differential signal based on the physiological signal received on the measurement electrode and/or the reference electrode. In some examples, as described with respect to FIGS. 6-7, measurement of a physiological signal can begin after a determination that the output of the first and second sensing circuit are not saturated.

At 810, the stimulation signal can optionally cease being driven on the measurement electrode. In some examples, driving the stimulation signal can be ceased in response to measuring the signal less than a threshold voltage. In some examples, step 810 is optional and the stimulation signal can be continued to be driven on the measurement electrode. At 812, in response to measuring the signal greater than a threshold voltage, the system can optionally stop measurement of a physiological signal. In some examples, while the stimulation signal is driven on the measurement electrode and after measurement of the physiological signal has begun, the system can determine that the signal generated in response to the stimulation signal is no longer less than a threshold voltage (e.g., is greater or equal to the threshold voltage). In some examples, when the system determines that the signal is no longer less than a threshold voltage, the system can cease measurement of the physiological signal. In some examples, this can include pausing the measurement and providing a notification (e.g., visual and/or audio and/or haptic feedback) for the user to resume contact with the measurement electrode. In some examples, after a threshold amount of time, pausing the measurement can time out and measurement can be aborted. In some examples, the physiological signal measured so far can be discarded. In some examples, ceasing measurement of the physiological signal can result from a determination that the measured signal no longer conforms to the characteristics of a physiological signal or can result from a determination that the measured signal is inconsistent with previously measured physiological signals (e.g., the signal has ended or the signal is subject to attenuation).

The description above primarily focuses on contact detection for one electrode (e.g., measurement electrode 502/

Figure 9:
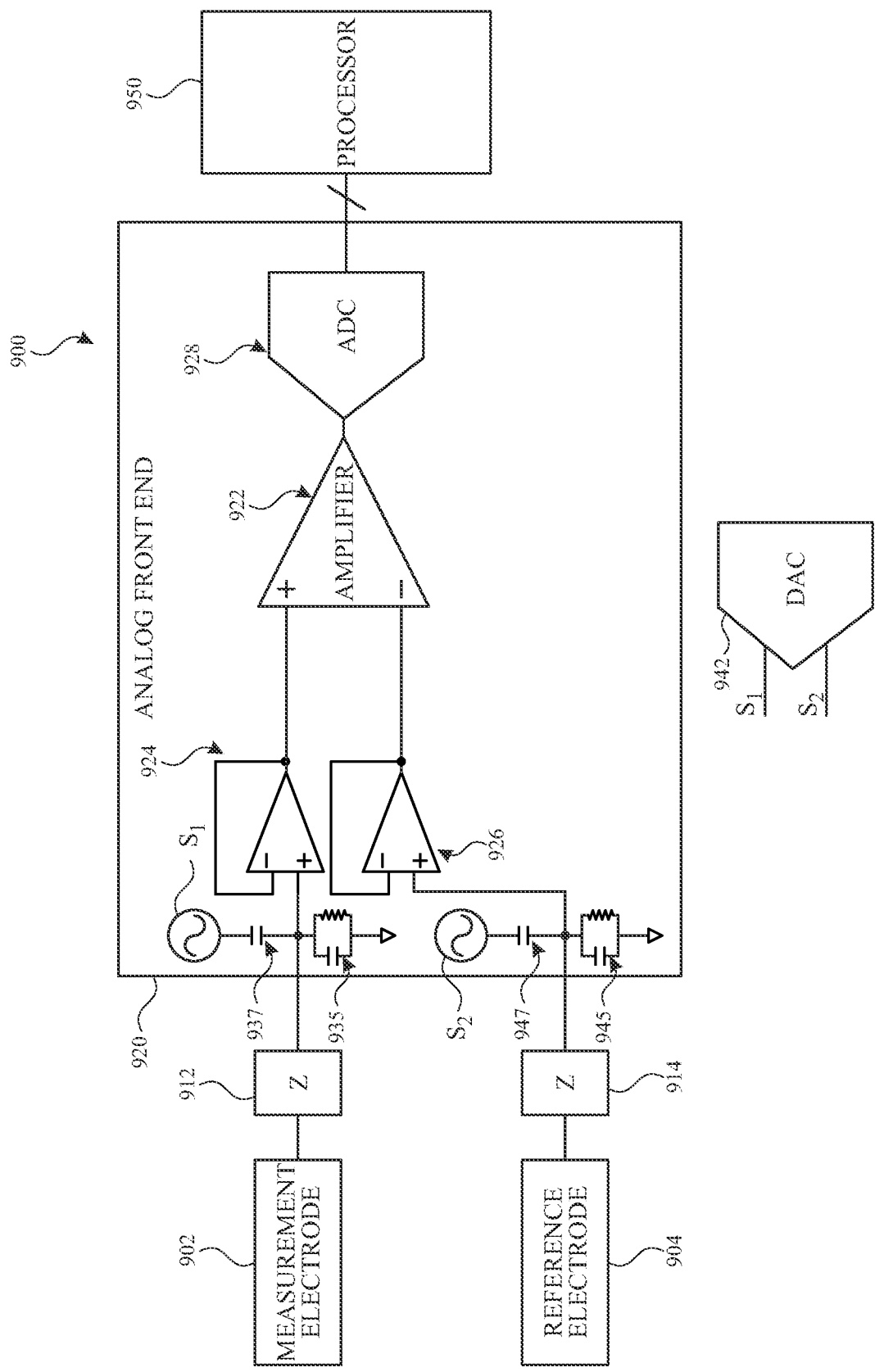
FIG. 9 illustrates an example system for measuring physiological signals and for contact detection on multiple electrodes according to examples of the disclosure.

602). In some examples, contact detection can be performed for multiple electrodes by driving a first stimulation signal on one of the electrodes (e.g., a first measurement electrode) and a second stimulation signal on a second of the electrodes (e.g., a second measurement electrode or a first reference electrode). Contact detection on multiple electrodes can be used to improve performance of physiological signal detection for systems including proper contact on two electrodes in a similar manner as described above for contact detection on one measurement electrode 502/602. FIG. 9 illustrates an example system for measuring physiological signals and for contact detection on multiple electrodes according to examples of the disclosure. Circuit 900 can be similar to circuits 500 and 600. Circuit 900 can include a first electrode (e.g., measurement electrode 902 corresponding to measurement electrode 502/602), a second electrode (e.g. reference electrode 904 corresponding to reference electrode 504/604), impedance networks 912 and 914 (e.g., corresponding to impedance networks 512/612 and 514/614), an analog front end circuit 920 (e.g., corresponding to analog front end 520 or 620) and a processor 950 (e.g., corresponding to processor 650). Analog front end circuit 920 can include buffers 924 and 926 (e.g., corresponding to buffers 524/624 and 526/626), differential amplifier 922 (e.g., corresponding to amplifier 522/622), and ADC 928 (e.g., corresponding to ADC 528/628). For ease of description, the saturation detection circuit 630 is omitted, but it should be understood that saturation detection can also be included as described herein for saturation detection.

Circuit 900 can also include test signal circuitry. However, unlike the illustration of circuits 500 and 600, the test signal circuitry can include circuitry to drive a first stimulation signal on a first electrode and a second stimulation signal (different from the first stimulation signal) on a second electrode (different from the first electrode). For example, the test signal circuitry can include a test signal generator including a digital to analog converter (DAC) 942 configured to output two complementary stimulation signals, S1 and S2. For example, S1 and S2 can be sinusoidal waves of the same frequency with 180 degree phase shift between S1 and S2. In some examples, DAC 942 can receive an oscillating signal and/or digital values from a memory to generate voltage values for the waveforms of S1 and S2. The first stimulation signal can be driven onto the first electrode via capacitor 937 and the second stimulation signal can be driven onto the second electrode via capacitor 947.

It should be understood that although S1 and S2 are described above as sinusoidal waves with a 180 degree phase shift, that in some examples, the first and/or second stimulation signals can be other waveforms (e.g., square wave, trapezoidal wave, saw-tooth wave or any other suitable wave), and/or the first and second stimulation signals can have a different phase relationship (e.g., 90 degree phase shift or any other suitable phase shift). Additionally, in some examples, the frequency of S1 and S2 can be the same or can be different (e.g., 1 kHz and 10 kHz). Finally, it should be understood that although DAC 942 is shown as generating both stimulation signals, that other circuitry can be used to generate the stimulation signals (two single-output DACs, or other test signal generator such as those described above with respect to FIGS. 5A-5B).

Circuit 900 can also include impedance networks 935 and 945 (e.g., similar to impedance networks 536/635) that can form voltage dividers with capacitors 937 and 947 for the two electrodes. The voltage of respective stimulation signals S1 and S2 can be divided by the respective voltage divider. In some examples, impedance networks 935 and 945 can include one or more discrete capacitors and/or one or more discrete resistors, and/or can represent parasitic impedances for each of the electrodes (modeling the electrode interface).

Buffer 924 can measure the node between capacitor 937 and impedance network 935 corresponding to the first electrode (e.g., measurement electrode 902). Buffer 926 can measure the node between capacitor 947 and impedance network 945 corresponding to the second electrode (e.g., reference electrode 904). The output of buffers 924 and 926 can be input to the two input terminals of differential amplifier 922. The output of differential amplifier 922 can represent a combination of the voltage at the node of the first electrode and the voltage at the node of the second electrode. For example, due to the complimentary nature of S1 and S2, the output of differential amplifier 922 can represent the sum of the voltages output by buffers 924 and 926 (subject to phase shifts introduced by the impedance changes due to electrical system and contact between the user and the electrode). For other non-complimentary stimulation signals, the differential amplifier can still combine outputs of buffers 924 and 926. The resulting output from differential amplifier 922 can, in some examples, have a sinusoidal waveform. The analog output from differential amplifier 922 can be digitized by ADC 928 and the digitized values can be sent to processor 950 for contact detection (e.g., in a similar manner as described with respect to FIGS. 7 and 8). It should be understood that although circuit 900 illustrated in FIG. 9 shows differential amplifier 922, it is understood that in some examples, differential amplifier 922 can be replaced by two single-end amplifiers and two separate ADCs (e.g., in a similar configuration as shown in independent contact detection circuit 1230 in FIG. 12).

For example, in a similar manner as described above, contact between a user and the first electrode can attenuate the output of buffer 924 (with respect to the output without contact) and contact between the user and the second electrode can attenuate the output of buffer 926 (with respect to the output without contact). The composite signal output from amplifier 922 can be evaluated to determine whether it meets one or more criteria. The one or more criteria can include a criterion that requires (e.g., that is satisfied when) the composite signal detected in response to the first and second stimulation is less than a threshold. When the composite digitized output of amplifier 922 is less than a threshold, processor 950 can determine proper contact between the user and both of the electrodes (e.g., sufficient contact to generate a physiological signal of threshold quality). When the composite digitized output of amplifier 922 is greater than the threshold, processor 950 can determine at least one improper contact between the user and one of the electrodes (e.g., insufficient contact to generate a physiological signal of threshold quality). As a result of detecting the composite digitized output is less than a threshold (corresponding to proper contact at two electrodes), the system can measure the physiological signal and/or continue measuring the physiological signal. As a result of detecting the composite digitized output is greater than the threshold (corresponding to improper contact at one or two electrodes), the system can forgo measuring a physiological signal and/or stop measuring the physiological signal (or discard the results or present a notification to the user, etc.), in a similar manner as described herein for contact detection for one measurement electrode.

As described herein, in some examples, the stimulation signals for contact detection can be continuously applied, periodically applied or may be applied in response to a trigger. In some examples, the contact detection can be performed continuously to indicate the quality of a physiological signal measurement during physiological signal measurement. In some examples, the contact detection can be used to trigger a physiological signal measurement session and/or terminate a physiological signal measurement session. In some examples, the contact detection can be used to differentiate between intended contact with a measurement electrode (e.g., on crown 162) from unintended contact with the measurement electrode (e.g., from a user's wrist). For example, contact between crown 162 and the user's wrist may be relatively intermittent (e.g., less than 3-5 seconds) compared with intended input for a physiological signal measurement that may require a threshold duration of contact (e.g., greater than 10 seconds). Thus, a session started due to unintended wrist contact may be terminated (and/or the session results can be discarded rather than displaying an inaccurate physiological signal measurement).

In order to perform contact detection continuously, in some examples, the stimulation frequency can be selected to be outside the frequency band used for physiological signal measurement. For example, as discussed herein, in some examples, the frequency of the stimulation signal(s) can be higher than the frequency of physiological signal. For example, the frequency spectrum of a physiological signal can be less than 150 Hz and the frequency of stimulation signal(s) can be 500 Hz, 600 Hz, or any other suitable frequency above 150 Hz. Additionally, using a sine wave rather than a square wave for the stimulation signal can improve separation of the frequency bands (as a square wave includes frequency content in multiple frequency ranges).

Figure 10:
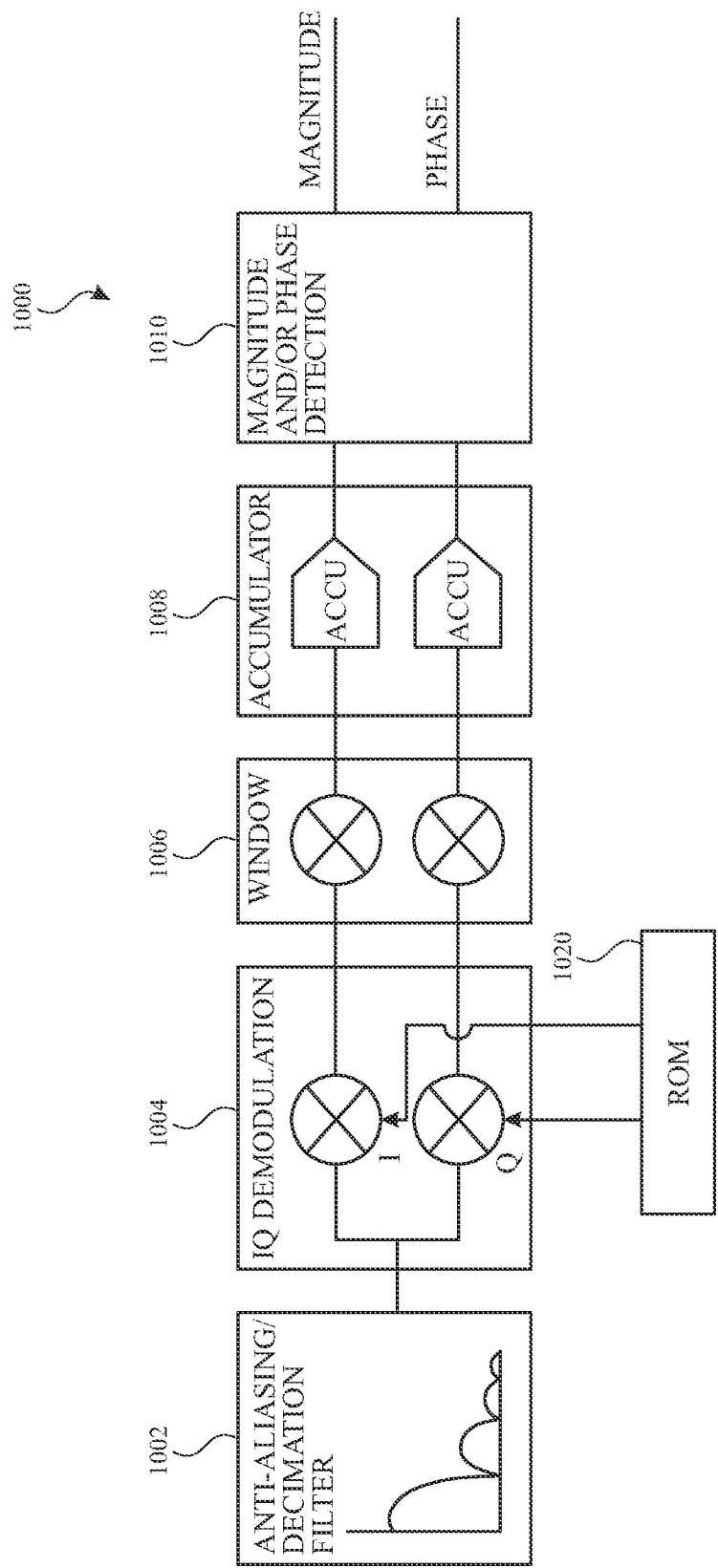
FIG. 10 illustrates exemplary signal processing for contact detection according to examples of the disclosure.

As described above, the digitized output of differential amplifier 922 can be processed for contact detection. In some examples, as described above, the contact detection can be based on an amplitude of the digitized output. In some examples, the contact detection can be based on impedance calculated from the digitized output (including magnitude and phase). The latter can be used to detect additional information regarding impedance. FIG. 10 illustrates exemplary signal processing block diagram 1000 for contact detection processing according to examples of the disclosure. In some examples, signal processing block diagram 1000 can be implemented in a digital signal processor or other processing circuit (e.g., DSP 206, processors 650/950, etc.), including, for example, application specific integrated circuits, programmable devices (field programmable gate array, programmable logic device, etc.) or software executed by a processor. In some examples, the digital signal processing for contact detection can operate on the output from analog front end circuit 920.

The digital signal processing can include a filter block 1002, an in-phase and quadrature (IQ) demodulation block 1004, a windowing block 1006, an accumulation block 1008, and a magnitude and/or phase detection block 1010. Filter block 1002 can optionally include a high-pass filter to remove high frequency noise and/or a low-pass filter such as a decimation/anti-aliasing filter. In some examples, a band-pass filter can be used to remove high frequency noise and low-frequency physiological signals. Although illustrated as filtering in the digital domain, it should be understood that in some implementations filtering can additionally or alternatively be performed in the analog domain (e.g., by analog front end circuitry 920). IQ demodulation block 1004 can include two mixers (e.g., signal multipliers) to mix the inputs to IQ demodulation block 1004 with an in-phase demodulation signal and a quadrature demodulation signal. For example, if stimulation signals S1 and S2 correspond to an in-phase sinusoid and a 180 degree out-of-phase sinusoid (e.g., at the same frequency), the in-phase demodulation signal can be the same as S1 and the quadrature demodulation signal can be a 90 degree phase-shifted version of S1. In some examples, the demodulation signals applied to the mixers can be stored in and provided from a memory (e.g., ROM 1020) to multiply by a digital sine wave, which can be stored in ROM memory (e.g., in or accessible by DSP 206). In some examples, the in-phase demodulation signal can be a delayed version of the in-phase stimulation signal (e.g., including a programmable delay added to account for differences in propagation through the system). In some examples, the quadrature demodulation signal can also be adjusted by a phase delay (e.g., using a programmable delay). The I component and Q component output by IQ demodulation block 1004 can be windowed by a windowing function at windowing block 1006. The windowing function applied at windowing block 1006 can include any suitable window including rectangular, Taylor, triangular, Hamming, Hanning, Gaussian, Kaiser, etc. The windowed I and Q components can be accumulated by accumulator block 1008. The windowed and accumulated I and Q components can be used to calculate the magnitude and/or phase at magnitude and/or phase detection block 1010. As described herein, the magnitude output can be calculated as $\sqrt{I^2+Q^2}$ and the phase can be calculated as $\tan^{-1} I/Q$ where I can represent the in-phase input to magnitude and/or phase detection block 1010 and Q can represent the quadrature input to magnitude and/or phase detection block 1010. As described herein, the magnitude can be proportional to the amplitude of the impedance and can be compared with a threshold to determine whether the user is sufficiently in contact with the electrode(s) or not.

It should be understood that the signal processing of FIG. 10 is an example signal processing, but that variations can be made without departing from the scope of the disclosure. For example, in some examples, the magnitude may be used for contact detection and it may be unnecessary to calculate the phase. Additionally or alternatively, some or all of the filtering can be moved to the analog domain. Additionally or alternatively, the IQ demodulation can be implemented in the analog domain. Additionally or alternatively, the window function can be implemented as part of the generation of the in-phase demodulation signal and the quadrature demodulation signal (e.g., the demodulation signals stored in ROM 1020 can be windowed or the window function can be applied to the output of ROM 1020 prior to IQ demodulation mixers). Additionally or alternatively, other demodulation techniques aside from IQ demodulation can be used.

In some examples, S1 and S2 can be stimulated at different frequencies and the signal processing of FIG. 10 can be performed for each stimulation signal frequency. For example, one signal corresponding to measurement electrode 902 stimulated with S1 at frequency f1 can be processed by the signal processing of FIG. 10, designed to capture frequency content at or near f1 (e.g., to filter frequency content at f2 in filter block 1002) to generate a magnitude and/or phase for measurement electrode 902. One signal corresponding to reference electrode 904 stimulated with S2 at frequency f2 (different from f1) can be similarly processed by the signal processing of FIG. 10, designed to capture frequency content at or near f2 (e.g., to filter out frequency content at f1 in filter block 1002) to generate a magnitude and/or phase for reference electrode 904. This processing can be time-multiplexed in processor 950 (applying different filtering at filter block 1002, different demodulation signals at IQ demodulation block 1004, etc.)

or processor 950 can include two signal processing channels to perform parallel processing (applying different filtering at filter block 1002, different demodulation signals at IQ demodulation block, etc.).

Figure 11:
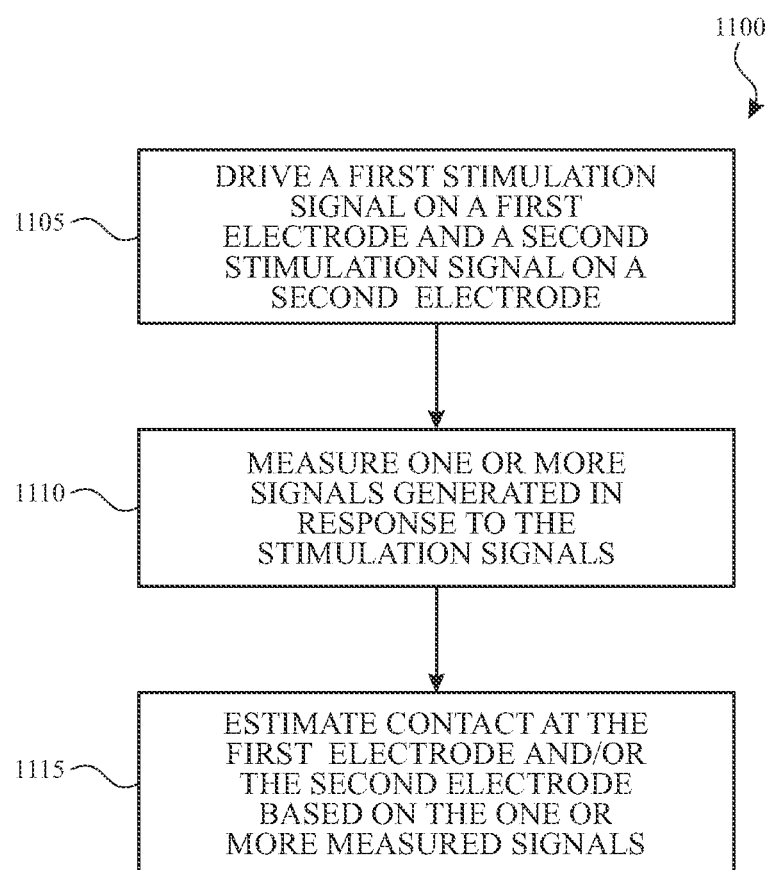
FIG. 11 illustrates an exemplary process of physiological signal detection including contact detection according to examples of the disclosure.

FIG. 11 illustrates an exemplary process of physiological signal detection including contact detection according to examples of the disclosure. Process 1100 can be performed by one or more processors of the system (e.g., DSP 206, host processor 208, processor 950, etc.) programmed to perform process 1100. At 1105, the system (e.g., DAC 942 controlled by processor 950) can drive a first stimulation signal (e.g., S1) on a first electrode (e.g., measurement electrode 902) and drive a second stimulation signal (S2) on a second electrode (e.g., reference electrode 904). As described above, S1 and S2 can be different stimulation signals. In some examples, S1 and S2 can be complementary stimulation signals with the same frequency, but 180 degrees out-of-phase. In some examples, the stimulation can be continuous, periodic or in response to a trigger (e.g., a user input requesting a physiological signal measurement, opening an application for measuring or viewing a physiological signal).

At 1110, the system (e.g., sense circuitry) can measure one or more signals generated in response to the stimulation signals. In some examples, the sense circuitry can include a first buffer coupled to a first electrode (e.g., buffer 924 coupled to measurement electrode 902) and a second buffer coupled to a second electrode (e.g., buffer 926 coupled to reference electrode 904). In some examples, measurement can be from the output of a differential amplifier (e.g., differential amplifier 922). At 1115, the system (e.g., processor 950) can estimate contact at the first electrode (e.g., measurement electrode 902) and/or at the second electrode (e.g., reference electrode 904). For example, the output of a differential amplifier 922 can be processed (e.g., according to signal processing in FIG. 10) to determine a magnitude. When the magnitude is less than a threshold (e.g., as determined by a processor, such as processor 950), the system can estimate contact between the user and the first electrode and the second electrode. As a result, the system can begin or continue measurement of a physiological signal. In some examples, beginning/continuing measuring the physiological signal can include acquiring the physiological signal (e.g., by data buffer 204 and/or DSP 206), storing the physiological signal (e.g., in program storage 210) and/or displaying the physiological signal on the display. In some examples, the physiological signal can be acquired from the measurement electrode and reference electrode via the sense circuitry (e.g., analog front end 920). In some examples, the physiological signal measurement can be a differential measurement between a measurement electrode and a reference electrode. For example, a differential amplifier (e.g., 922) can output a differential signal based on the physiological signal received on the measurement electrode and/or the reference electrode. In some examples, as described with respect to FIGS. 6-7, measurement of a physiological signal can begin after a determination that the output of the first and second sensing circuit are not saturated.

When the magnitude is greater than the threshold (e.g., as determined by a processor, such as processor 950), the system can estimate contact is weak or broken between the user and the first electrode and/or the second electrode. In some examples, in response to measuring the signal greater than a threshold voltage, measurement of a physiological signal can be stopped. In some examples, this can include pausing the measurement and providing a notification (e.g., visual and/or audio and/or haptic feedback) for the user to resume contact with the electrode(s). In some examples, after a threshold amount of time, pausing the measurement can time out and measurement can be aborted. In some examples, the physiological signal measured so far can be discarded.

Although process 1100 is described as estimating contact with the first measured electrode and/or the second measurement electrode, it is understood that the system may take action (e.g., starting/continuing/terminating/pausing/discarding a physiological signal measurement) in accordance with the measured signal magnitude being greater than or less than a threshold, without making an estimate of contact. However, the threshold can be set such that the signal below the threshold indicates contact (e.g., sufficient contact for a physiological signal measurement of a threshold quality) on multiple electrodes and signal above the threshold indicates a break in contact or weak contact (e.g., insufficient contact for a physiological signal measurement of a threshold quality) on one or multiple electrodes.

In some examples, S1 and S2 can be at different frequencies. In some such examples, the processing at 1115 can include separately estimating contact at the first electrode (e.g., measurement electrode 902) and contact at the second electrode (e.g., reference electrode 904). For example, the output of a differential amplifier 922 can be processed (e.g., according to signal processing in FIG. 10) for different frequencies to determine a magnitude for electrode (as described herein). When the magnitude is less than a threshold for a respective electrode (e.g., as determined by a processor, such as processor 950), the system can estimate contact between the user and the respective electrode. When the magnitude is greater than the threshold for a respective electrode (e.g., as determined by a processor, such as processor 950), the system can estimate poor contact or a lack of contact between the user and the respective electrode. The system can begin or continue measurement of a physiological signal when proper contact is established for both electrodes (e.g., when both are less than the threshold). When the magnitude is greater than the threshold for either respective contact, measurement of a physiological signal can be stopped. In some examples, this can include pausing the measurement and providing a notification (e.g., visual and/or audio and/or haptic feedback) for the user to resume contact with the electrode(s). In some examples, the notifications provided to the user can change to provide the user better information about which contact to improve (e.g., instruct the user to improve contact on crown 162/measurement electrode 166C when there is poor user contact with the crown, tighten strap 154 when there is poor user contact with a reference electrode 166A/166B, or both when there are contact problems with both).

FIG. 12 illustrates an example system for measuring physiological signals and for contact detection on multiple electrodes according to examples of the disclosure. Circuit 1200 can be similar to circuits 900, including a first electrode (e.g., measurement electrode 1202 corresponding to measurement electrode 902), a second electrode (e.g. reference electrode 1204 corresponding to reference electrode 904), impedance networks 1212 and 1214 (e.g., corresponding to impedance networks 912 and 914), an analog front end circuit 1220 (e.g., corresponding to analog front end 920) and a processor 1250 (e.g., corresponding to processor 950). Analog front end circuit 1220 can include buffers 1224 and 1226 (e.g., corresponding to buffers 924 and 926), differential amplifier 1222 (e.g., corresponding to amplifier 922), and ADC 1228 (e.g., corresponding to ADC 928).

Circuit 1200 can also include test signal circuitry (e.g., DAC 1242 corresponding to DAC 942, coupling capacitors 1237 and 1247 corresponding to capacitors 937 and 947, and impedance networks 1235 and 1245 corresponding to impedance networks 935 and 945).

Additionally, in order to separately perform contact detection (and/or impedance measurements) for multiple contacts, analog front end circuit 1220 can also include the independent contact detection circuit 1230. Saturation detection circuitry is omitted for ease of description, but it should be understood that saturation detection can also be included as described herein for saturation detection (and in some examples, the same circuitry can be used for independent contact detection and for saturation detection).

Independent contact detection circuit 1230 can include, in some examples, buffers 1234 and 1236, multiplexer 1232, and analog-to-digital converter 1238. In some examples, buffers 1234 and 1236 are coupled to route signals from measurement electrode 1202 and reference electrode 1204, respectively, to multiplexer 1232. In some examples, multiplexer 1232 multiplexes between selecting the signal from measurement electrode 1202 to pass through to processor 1250 and selecting the signal from reference electrode 1204 to pass through to processor 1250. In some examples, processor 1250 can control the multiplexing of multiplexer 1232. In some examples, analog-to-digital converter 1238 converts the analog signal from multiplexer 1232 to a digital signal. In some examples, the digital signal is then input to processor 1250. In some examples, the digital output of analog-to-digital converter 1238 can be a multi-bit signal (e.g., 4 bits, 6 bits, 8 bits, 10 bits, 12 bits, etc.). In some examples, the digital output of analog-to-digital converter 1238 can have fewer bits than analog-to-digital converter 1228, as the precision of the measurement for contact detection may be less than for measuring the physiological signal. In some examples, rather than time-multiplexing the measurement of signals for contact detection, multiplexer 1232 can be omitted and each of buffers 1234 and 1236 can be coupled to its own ADC (not shown).

The signals from independent contact detection circuit 1230 can be processed by processor 1250. In some examples, one signal corresponding to measurement electrode 1202 and buffer 1234 can be processed by the signal processing of FIG. 10 to generate a magnitude and/or phase shift for measurement electrode 1202. In some examples, one signal corresponding to reference electrode 1204 and buffer 1236 can similarly be processed by the signal processing of FIG. 10 to generate a magnitude and/or phase shift for reference electrode 1204. This processing can be time-multiplexed in processor 1250 or processor 1250 can include two signal processing channels to perform parallel processing. The magnitude information for each electrode can be compared with a threshold (e.g., in a similar manner as described herein for the differential output of differential amplifier 922) to determine/estimate whether each electrode is contacted. For example, contact between a user and the first electrode can attenuate the output of buffer 1224 (with respect to the output without contact) and contact between the user and the second electrode can attenuate the output of buffer 1226 (with respect to the output without contact).

The separate processing of FIG. 12 can allow for determining whether a break in contact (or poor contact) is detected at the first electrode (e.g., measurement electrode 1202) or at the second electrode (e.g., reference electrodes 1204) or both. In some examples, the notifications provided to the user can change to provide the user better information about which contact to improve (e.g., instruct the user to improve contact on crown 162/measurement electrode 166C when there is poor user contact with the crown, tighten strap 154 when there is poor user contact with a reference electrode 166A/166B, or both when there are contact problems with both).

As discussed above, aspects in of the present technology include the gathering and use of physiological information. The technology may be implemented along with technologies that involve gathering personal data that relates to the user's health and/or uniquely identifies or can be used to contact or locate a specific person. Such personal data can include demographic data, date of birth, location-based data, telephone numbers, email addresses, home addresses, and data or records relating to a user's health or level of fitness (e.g., vital signs measurements, medication information, exercise information, etc.).

The present disclosure recognizes that a user's personal data, including physiological information, such as data generated and used by the present technology, can be used to the benefit of users. For example, a user's heart rate may allow a user to track or otherwise gain insights about their health or fitness levels.

The present disclosure contemplates that the entities responsible for the collection, analysis, disclosure, transfer, storage, or other use of such personal data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should require receipt of the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. The policies and practices may be adapted depending on the geographic region and/or the particular type and nature of personal data being collected and used.

Despite the foregoing, the present disclosure also contemplates embodiments in which users selectively block the collection of, use of, or access to, personal data, including physiological information. For example, a user may be able to disable hardware and/or software elements that collect physiological information. Further, the present disclosure contemplates that hardware and/or software elements can be provided to prevent or block access to personal data that has already been collected. Specifically, users can select to remove, disable, or restrict access to certain health-related applications collecting users' personal health or fitness data Therefore, according to the above, some examples of the disclosure are directed a device. The device can comprise sensing circuitry configured to sense a physiological signal, the sensing circuitry including a first sensing circuit configured to sense a first electrode and a second sensing circuit configured to sense a second electrode; a stimulation circuit configured to drive a stimulation signal on the first electrode; and processing circuitry coupled to the sensing circuitry, the processing circuitry configured to (e.g., programmed to):

detect one or more signals measured by the first sensing circuit, wherein at least one signal of the one or more signals is measured by the first sensing circuit in response to the stimulation signal; detect one or more signals measured by the second sensing circuit; in accordance with the one or more signals measured by the first sensing circuit and the one or more signals measured by the second sensing circuit meeting one or more criteria, measure the physiological signal; and in accordance with the one or more signals measured by the first sensing circuit and the one or more signals measured by the second sensing circuit failing to meet the one or more criteria, forgo measuring the physiological signal.

Additionally or alternatively, in some examples, the one or more criteria can include a first criterion that requires the at least one signal measured in response to the stimulation signal has an amplitude less than a threshold voltage. Additionally or alternatively, in some examples, the stimulation circuit can comprise: a signal generator configured to generate the stimulation signal; and a capacitor configured to couple the stimulation signal to the first electrode. Additionally or alternatively, in some examples, the stimulation signal can be a periodic oscillating signal. Additionally or alternatively, in some examples, the stimulation signal can have a frequency greater than 40 Hz. Additionally or alternatively, in some examples, the stimulation signal can have a frequency between 100 Hz and 600 Hz. Additionally or alternatively, in some examples, the sensing circuitry can further comprise a differential analog-to-digital converter (ADC) configured to convert differential analog output of the differential amplifier into a digital output. Additionally or alternatively, in some examples, the sensing circuitry can further comprise two single-ended amplifiers and two single-ended analog-to-digital converters (ADC) configured to convert analog output of the two single-ended amplifiers into digital outputs. Additionally or alternatively, in some examples, the sensing circuitry can further comprise a saturation detection circuit coupled to an output of the first sensing circuit and an output of the second sensing circuit, wherein the saturation detection circuit is configured to detect saturation of the output of the first sensing circuit or of the output of the second sensing circuit.

Additionally or alternatively, in some examples, the saturation detection circuit can comprise: a first buffer coupled to the output of the first sensing circuit; a second buffer coupled to the output of the second sensing circuit; a multiplexer coupled to the first buffer and the second buffer, wherein an output of the first buffer and an output of the second buffer are coupled as inputs to the multiplexer; and an analog-to-digital converter (ADC). Additionally or alternatively, in some examples, the one or more criteria can include a second criterion that requires the output of the first sensing circuit and the output of the second sensing circuit are not saturated. Additionally or alternatively, in some examples, the sensing circuitry can further include a differential amplifier, wherein an output of the first sensing circuit is coupled to a first input (e.g., inverting input) of the differential amplifier and wherein an output of the second sensing circuit is coupled to a second input (e.g., non-inverting input) of the differential amplifier.

Additionally or alternatively, in some examples, the processing circuitry can be further configured to: in accordance with the at least one signal of the one or more signals measured by the first sensing circuit in response to the stimulation signal meeting the one or more criteria, cease driving the stimulation signal. Additionally or alternatively, in some examples, the processing circuitry can be further configured to: determine, while measuring the physiological signal, that at least one signal of the one or more signals measured by the first circuit in response to the stimulation signal fails to meet the one or more criteria; and in response to determining that the at least one signal of the one or more signals measured by the first circuit in response to the stimulation signal fails to meet the one or more criteria, cease measuring the physiological signal. Additionally or alternatively, in some examples, the stimulation circuit can be driving the stimulation signal on the first electrode while measuring the physiological signal. Additionally or alternatively, in some examples, measuring the physiological signal can comprise: filtering the one or more signals measured by the sensing circuitry to remove the at least one signal measured in response to the stimulation signal from the one or more signals.

Some examples of the disclosure are directed to a method. The method can comprise receiving a user input requesting a physiological signal measurement; in response to receiving the user input, driving a first measurement electrode with a stimulation signal; measuring one or more signals, wherein at least one signal of the one or more signals is measured in response to the stimulation signal; in accordance with the one or more signals meeting one or more criteria, the one or more criteria including a criterion that requires the at least one signal measured in response to the stimulation signal has an amplitude less than a threshold voltage, performing the physiological signal measurement; and in accordance with the one or more signals failing to meet the one or more criteria, forgoing the physiological signal measurement.

Additionally or alternatively, in some examples, the stimulation signal can be a periodic oscillating signal. Additionally or alternatively, in some examples, the stimulation signal can have a frequency greater than 40 Hz. Additionally or alternatively, in some examples, the stimulation signal can have a frequency between 100 Hz and 600 Hz. Additionally or alternatively, in some examples, the method can further comprise detecting saturation of an output of a first sensing circuit coupled to the first measurement electrode or saturation of an output of a second sensing circuit coupled to a reference electrode. Additionally or alternatively, in some examples, the one or more criteria includes a criterion that requires the output of the first sensing circuit and the output of the second sensing circuit are not saturated.

Additionally or alternatively, in some examples, the method can further comprise: in accordance with the one or more signals meeting one or more criteria, ceasing driving the first measurement electrode with the stimulation signal. Additionally or alternatively, in some examples, the method can further comprise: determining, while performing the physiological signal measurement, that the at least one signal of the one or more signals measured in response to the stimulation signal has an amplitude not less than the threshold voltage; and in response to determining that the at least one signal of the one or more signals measured in response to the stimulation signal has an amplitude not less than the threshold voltage, ceasing performing the physiological signal measurement. Additionally or alternatively, in some examples, the first measurement electrode can be driven with the stimulation signal while performing the physiological signal measurement. Additionally or alternatively, in some examples, performing the physiological signal measurement can comprise: filtering the one or more signals measured by the sensing circuitry to remove the at least one signal measured in response to the stimulation signal from the one or more signals.

Some examples of the disclosure are directed to non-transitory computer readable storage medium. The non-transitory computer readable storage medium can store instructions, which when executed by a device comprising a first measurement electrode and one or more processing circuits, cause the one or more processing circuits to perform a method. In some examples, the method can comprise receiving a user input requesting a physiological signal measurement; in response to receiving the user input, driving a first measurement electrode with a stimulation signal; measuring one or more signals, wherein at least one signal of the one or more signals is measured in response to the stimulation signal; in accordance with the one or more signals meeting one or more criteria, the one or more criteria including a criterion that requires the at least one signal measured in response to the stimulation signal has an amplitude less than a threshold voltage, performing the physiological signal measurement; and in accordance with the one or more signals failing to meet the one or more criteria, forgoing the physiological signal measurement.

Additionally or alternatively, in some examples, the stimulation signal can be a periodic oscillating signal. Additionally or alternatively, in some examples, the stimulation signal can have a frequency greater than 40 Hz. Additionally or alternatively, in some examples, the stimulation signal can have a frequency between 100 Hz and 600 Hz. Additionally or alternatively, in some examples, the method can further comprise detecting saturation of an output of a first sensing circuit coupled to the first measurement electrode or saturation of an output of a second sensing circuit coupled to a reference electrode. Additionally or alternatively, in some examples, the one or more criteria includes a criterion that requires the output of the first sensing circuit and the output of the second sensing circuit are not saturated.

Additionally or alternatively, in some examples, the method can further comprise: in accordance with the one or more signals meeting one or more criteria, ceasing driving the first measurement electrode with the stimulation signal. Additionally or alternatively, in some examples, the method can further comprise: determining, while performing the physiological signal measurement, that the at least one signal of the one or more signals measured in response to the stimulation signal has an amplitude not less than the threshold voltage; and in response to determining that the at least one signal of the one or more signals measured in response to the stimulation signal has an amplitude not less than the threshold voltage, ceasing performing the physiological signal measurement. Additionally or alternatively, in some examples, the first measurement electrode can be driven with the stimulation signal while performing the physiological signal measurement. Additionally or alternatively, in some examples, performing the physiological signal measurement can comprise: filtering the one or more signals measured by the sensing circuitry to remove the at least one signal measured in response to the stimulation signal from the one or more signals.

Some examples of the disclosure are directed a device. The device can comprise sensing circuitry configured to sense a physiological signal, the sensing circuitry including a first sensing circuit configured to sense a first electrode and a second sensing circuit configured to sense a second electrode; a stimulation circuit configured to drive a first stimulation signal on the first electrode and configured to drive a second stimulation signal on the second electrode; and processing circuitry coupled to the sensing circuitry. The processing circuitry can be programmed to: in accordance with one or more signals measured in response to the first stimulation signal and the second stimulation signal meeting one or more criteria, measure the physiological signal; and in accordance with the one or more signals measured in response to the first stimulation signal and the second stimulation signal failing to meet the one or more criteria, forgo measuring the physiological signal. Additionally or alternatively, in some examples, the sensing circuitry can further include a differential amplifier. An output of the first sensing circuit can be coupled to a first input of the differential amplifier and an output of the second sensing circuit can be coupled to a second input of the differential amplifier. The one or more signals measured in response to the first stimulation signal and the second stimulation signal can be output by an output of the differential amplifier. Additionally or alternatively, in some examples, the one or more criteria can include a first criterion that can be satisfied when the one or more signals measured in response to the first stimulation signal and the second stimulation signal have an amplitude less than a threshold voltage. Additionally or alternatively, in some examples, the one or more signals measured in response to the first stimulation signal and the second stimulation signal can comprise one or more first signals measured by the first sensing circuit and one or more second signals measured by the second sensing circuit. Additionally or alternatively, in some examples, the one or more criteria can include a first criterion that can be satisfied when the one or more first signals measured in response to the first stimulation signal have an amplitude less than a threshold voltage and a second criterion that can be satisfied when the one or more second signals measured in response to second stimulation signal have an amplitude less than the threshold voltage. Additionally or alternatively, in some examples, the stimulation circuit can comprise: a signal generator configured to generate the first stimulation signal and the second stimulation signal; a first capacitor configured to couple the first stimulation signal to the first electrode; and a second capacitor configured to couple the second stimulation signal to the second electrode. Additionally or alternatively, in some examples, the signal generator can comprise a digital to analog converter. Additionally or alternatively, in some examples, the first stimulation signal can be a periodic oscillating signal with a first frequency and a first phase and the second stimulation signal can be a periodic oscillating signal with the first frequency and a second phase, different than the first phase. Additionally or alternatively, in some examples, the first phase and the second phase can be separated by 180 degrees. Additionally or alternatively, in some examples, the first frequency can be greater than 150 Hz. Additionally or alternatively, in some examples, the first stimulation signal and the second stimulation signal can be driven concurrently. Additionally or alternatively, in some examples, the first stimulation signal and the second stimulation signal can be driven at least partially concurrently with measuring the physiological signal. Additionally or alternatively, in some examples, the first stimulation signal can be a periodic oscillating signal with a first frequency and the second stimulation signal can be a periodic oscillating signal with the second frequency, different than the first frequency. Additionally or alternatively, in some examples, the first frequency and the second frequency can be greater than 150 Hz. Additionally or alternatively, in some examples, the processing circuitry can be further programmed to: determine, while measuring the physiological signal, that the at least one signal of the one or more signals measured in response to the first stimulation signal and the second stimulation signal fails to meet the one or more criteria; and in response to determining that the at least one signal of the one or more signals measured in response to the first stimulation signal and the second stimulation fails to meet the one or more criteria, cease measuring the physiological signal. Additionally or alternatively, in some examples, measuring the physiological signal can comprise: filtering one or more signals measured by the sensing circuitry to remove the one or more signals measured in response to the first stimulation signal and the second stimulation signal from the one or more signals. Additionally or alternatively, in some examples, the processing circuitry can be further programmed to: filter the one or more signals measured in response to the first stimulation signal and the second stimulation signal; demodulate the one or more signals measured in response to the first stimulation signal and the second stimulation signal; window the one or more signals measured in response to the first stimulation signal and the second stimulation signal; and/or compute an amplitude of the one or more signals measured in response to the first stimulation signal and the second stimulation signal. Additionally or alternatively, in some examples, the processing circuitry can be further programed to: demodulate the one or more signals measured in response to the first stimulation signal and the second stimulation signal with a first demodulation signal and a second demodulation signal, the second demodulation signal 90 degrees out of phase with the first demodulation signal. A frequency of the first stimulation signal and the second stimulation signal can be the same as a frequency of first demodulation signal and the second demodulation signal.

Some examples of the disclosure are directed to a method. The method can comprise: driving a first stimulation signal on a first electrode and a second stimulation signal on a second electrode, different from the first electrode; measuring one or more signals in response to the first stimulation signal and the second stimulation signal; in accordance with the one or more signals measured in response to the first stimulation signal and the second stimulation signal meeting one or more criteria, measuring a physiological signal; and in accordance with the one or more signals measured in response to the first stimulation signal and the second stimulation signal failing to meet the one or more criteria, forgoing measuring the physiological signal. Additionally or alternatively, in some examples, measuring the one or more signals in response to the first stimulation signal and the second stimulation signal can comprise: measuring the first electrode with a first sensing circuit; and measuring the second electrode with a second sensing circuit. The one or more signals measured in response to the first stimulation signal and the second stimulation signal can be outputs of a differential amplifier that receives outputs of the first sensing circuit and second sensing circuit. Additionally or alternatively, in some examples, the one or more criteria can include a first criterion that can be satisfied when the one or more signals measured in response to the first stimulation signal and the second stimulation signal have an amplitude less than a threshold voltage. Additionally or alternatively, in some examples, the one or more signals measured in response to the first stimulation signal and the second stimulation signal can comprise one or more first signals measured by a first sensing circuit coupled to the first electrode and one or more second signals measured by a second sensing circuit coupled to the second electrode. Additionally or alternatively, in some examples, the one or more criteria can include a first criterion that can be satisfied when the one or more first signals measured in response to the first stimulation signal have an amplitude less than a threshold voltage and a second criterion that can be satisfied when the one or more second signals measured in response to second stimulation signal have an amplitude less than the threshold voltage. Additionally or alternatively, in some examples, driving the first stimulation signal on the first electrode and the second stimulation signal on the second electrode can comprise coupling the first stimulation signal to the first electrode via a first capacitor and coupling the second stimulation signal to the second electrode via a second capacitor. Additionally or alternatively, in some examples, the first stimulation signal can be a periodic oscillating signal with a first frequency and a first phase and the second stimulation signal can be a periodic oscillating signal with the first frequency and a second phase, different than the first phase. Additionally or alternatively, in some examples, the first phase and the second phase can be separated by 180 degrees. Additionally or alternatively, in some examples, the first frequency can be greater than 150 Hz. Additionally or alternatively, in some examples, the first stimulation signal and the second stimulation signal can be driven concurrently. Additionally or alternatively, in some examples, the first stimulation signal and the second stimulation signal can be driven at least partially concurrently with measuring the physiological signal. Additionally or alternatively, in some examples, the first stimulation signal can be a periodic oscillating signal with a first frequency and the second stimulation signal can be a periodic oscillating signal with the second frequency, different than the first frequency. Additionally or alternatively, in some examples, the first frequency and the second frequency can be greater than 150 Hz. Additionally or alternatively, in some examples, the method can further comprise: determining, while measuring the physiological signal, that at least one signal of the one or more signals measured in response to the first stimulation signal and the second stimulation signal fails to meet the one or more criteria; and in response to determining that the at least one signal of the one or more signals measured in response to the first stimulation signal and the second stimulation fails to meet the one or more criteria, ceasing measuring the physiological signal. Additionally or alternatively, in some examples, measuring the physiological signal can comprise filtering one or more signals measured by sensing circuitry to remove the one or more signals measured in response to the first stimulation signal and the second stimulation signal from the one or more signals. Additionally or alternatively, in some examples, the method can further comprise: filtering the one or more signals measured in response to the first stimulation signal and the second stimulation signal; demodulating the one or more signals measured in response to the first stimulation signal and the second stimulation signal; windowing the one or more signals measured in response to the first stimulation signal and the second stimulation signal; and/or computing an amplitude of the one or more signals measured in response to the first stimulation signal and the second stimulation signal. Additionally or alternatively, in some examples, the method can further comprise: demodulating the one or more signals measured in response to the first stimulation signal and the second stimulation signal with a first demodulation signal and a second demodulation signal, the second demodulation signal 90 degrees out of phase with the first demodulation signal. A frequency of the first stimulation signal and the second stimulation signal can be the same as a frequency of first demodulation signal and the second demodulation signal.

Some examples of the disclosure are directed to non-transitory computer readable storage medium. The non-transitory computer readable storage medium can store instructions, which when executed by a device comprising a first electrode, a second electrode and one or more processing circuits, cause the one or more processing circuits to perform any of the above methods.

Although examples of this disclosure have been fully described with reference to the accompanying drawings, it is to be noted that various changes and modifications will become apparent to those skilled in the art. Such changes and modifications are to be understood as being included within the scope of examples of this disclosure as defined by the appended claims.

The invention claimed is:

1. A device comprising:
   sensing circuitry configured to sense a physiological signal, the sensing circuitry including a first sensing circuit configured to sense a first electrode and a second sensing circuit configured to sense a second electrode;
   a stimulation circuit configured to drive a stimulation signal on the first electrode; and
   processing circuitry coupled to the sensing circuitry, the processing circuitry programmed to, while measuring the physiological signal using one or more signals measured by the first sensing circuit and using one or more signals measured by the second sensing circuit:
      in accordance with a determination that a first signal of the one or more signals measured by the first sensing circuit in response to the stimulation signal fails to meet one or more criteria, cease measuring the physiological signal.

2. The device of claim 1, the processing circuitry further programmed to, while measuring the physiological signal:
   in accordance with a determination that the first signal of the one or more signals measured by the first sensing circuit in response to the stimulation signal meets the one or more criteria, continue measuring the physiological signal.

3. The device of claim 2, wherein the processing circuitry is further programmed to:
   in accordance with the determination that the first signal of the one or more signals measured by the first sensing circuit in response to the stimulation signal meets the one or more criteria, cease driving the stimulation signal.

4. The device of claim 1, wherein the one or more criteria includes a first criterion that is met when the first signal of the one or more signals measured by the first sensing circuit in response to the stimulation signal has an amplitude less than a threshold voltage.

5. The device of claim 1, wherein the stimulation circuit comprises:
   a signal generator configured to generate the stimulation signal; and
   a capacitor configured to couple the stimulation signal to the first electrode.

6. The device of claim 1, wherein the stimulation signal is a periodic oscillating signal.

7. The device of claim 1, wherein the stimulation signal has a frequency greater than 150 Hz.

8. The device of claim 1, wherein the stimulation signal has a frequency between 400 Hz and 600 Hz.

9. The device of claim 1, wherein the sensing circuitry further includes a differential amplifier, wherein an output of the first sensing circuit is coupled to a first input of the differential amplifier and wherein an output of the second sensing circuit is coupled to a second input of the differential amplifier.

10. The device of claim 9, wherein the sensing circuitry further comprises a differential analog-to-digital converter (ADC) coupled to an output of the differential amplifier.

11. The device of claim 1, wherein the stimulation circuit is configured to drive the stimulation signal on the first electrode while measuring the physiological signal.

12. The device of claim 1, wherein the processing circuitry is further programmed to:
   filter the first signal of the one or more signals measured by the first sensing circuit in response to the stimulation signal from the one or more signals measured by the first sensing circuit.

13. A non-transitory computer readable storage medium storing instructions, which when executed by a device comprising a first measurement electrode and processing circuitry, cause the device to:
   in accordance with a request to measure a physiological signal, initiate measuring the physiological signal and drive the first measurement electrode with a stimulation signal, wherein measuring the physiological signal and driving the first measurement electrode with the stimulation signal overlap at least partially in time;
   measure a plurality of signals, wherein a first signal of the plurality of signals is measured in response to the stimulation signal; and
   in accordance with a determination that an amplitude of the first signal measured in response to the stimulation signal is above a threshold voltage, cease measuring the physiological signal.

14. The non-transitory computer readable storage medium of claim 13, wherein the instructions, when executed by the device, further cause the device to:
   filter the first signal of the plurality of signals in response to the stimulation signal from the plurality of signals.

15. The non-transitory computer readable storage medium of claim 13, wherein the instructions, when executed by the device, further cause the device to:
   in accordance with the determination that the amplitude of the first signal measured in response to the stimulation signal is above the threshold voltage, cease driving the stimulation signal.

16. The non-transitory computer readable storage medium of claim 13, wherein the stimulation signal is a periodic oscillating signal with a frequency greater than 40 Hz.

17. The non-transitory computer readable storage medium of claim 13, wherein the instructions, when executed by the device, further cause the device to, while measuring the physiological signal:
   in accordance with a determination that the amplitude of the first signal measured in response to the stimulation signal is below the threshold voltage, continue measuring the physiological signal.

18. A device comprising:
   sensing circuitry configured to sense a physiological signal, the sensing circuitry including:
      a first sensing circuit configured to sense a first electrode;
      a second sensing circuit configured to sense a second electrode; and
      a saturation detection circuit coupled to an output of the first sensing circuit and an output of the second sensing circuit, wherein the saturation detection circuit is configured to detect saturation of the output of the first sensing circuit or of the output of the second sensing circuit; and
   processing circuitry coupled to the sensing circuitry, the processing circuitry programmed to:

in accordance with a determination that the output of the first sensing circuit or the output of the second sensing circuit is saturated, forgo measuring the physiological signal.

19. The device of claim 18, wherein the saturation detection circuit comprises:
- a first buffer coupled to the output of the first sensing circuit;
- a second buffer coupled to the output of the second sensing circuit;
- a multiplexer coupled to the first buffer and the second buffer, wherein an output of the first buffer and an output of the second buffer are coupled as inputs to the multiplexer; and
- an analog-to-digital converter (ADC) coupled to an output of the multiplexer.

20. The device of claim 18, wherein the saturation detection circuit comprises:
- a first buffer coupled to the output of the first sensing circuit;
- a second buffer coupled to the output of the second sensing circuit;
- a first analog-to-digital converter (ADC) coupled to an output of the first buffer; and
- a second ADC coupled to an output of the second buffer.

* * * * *